US008163019B2

(12) United States Patent
Bao et al.

(10) Patent No.: US 8,163,019 B2
(45) Date of Patent: Apr. 24, 2012

(54) IMPLANT RESTRAINT DEVICE AND METHODS

(75) Inventors: Qi-Bin Bao, Marquette, MI (US); Brian P. Janowski, Marquette, MI (US); Thomas S. Kilpela, Marquette, MI (US); John Sullivan, Marquette, MI (US); Jeffrey L. Trudeau, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 594 days.

(21) Appl. No.: 11/963,745

(22) Filed: Dec. 21, 2007

(65) Prior Publication Data

US 2008/0249623 A1 Oct. 9, 2008

Related U.S. Application Data

(60) Provisional application No. 60/871,641, filed on Dec. 22, 2006, provisional application No. 60/948,273, filed on Jul. 6, 2007.

(51) Int. Cl.
*A61F 2/44* (2006.01)
(52) U.S. Cl. .................................. 623/17.11
(58) Field of Classification Search ..... 623/17.11–17.16
See application file for complete search history.

(56) References Cited

U.S. PATENT DOCUMENTS

| 3,805,775 A * | 4/1974 | Fischer et al. ............... 606/68 |
| 5,702,468 A | 12/1997 | Goldberg |
| 5,782,866 A | 7/1998 | Wenstrom |
| 6,113,638 A | 9/2000 | William et al. |
| 6,200,330 B1 | 3/2001 | Benderev et al. |

(Continued)

FOREIGN PATENT DOCUMENTS
WO 2006044649 4/2006
(Continued)

OTHER PUBLICATIONS

International Search Report dated Jul. 18, 2009, from corresponding International Patent Application No. PCT/US2007/088744.

*Primary Examiner* — Eduardo C Robert
*Assistant Examiner* — Summer Kostelnik
(74) *Attorney, Agent, or Firm* — Fitch, Even, Tabin & Flannery, LLP

(57) ABSTRACT

An implant retention device is provided to assist in restraining movement of a nuclear implant and to assist in preventing expulsion of the nuclear implant through an incision portal or defect in the annular wall. In general, the implant retention device blocks or obstructs at least a portion of an opening in the annular wall, thereby keeping the implant from exiting the nuclear space through the annular opening. In one form, the implant retention device comprises an expulsion prevention member positioned adjacent the nuclear implant and configured to transition between a compressed position and an expanded position. In another form, the implant retention device may comprise a mounting portion to be positioned adjacent one of the vertebral bodies, a blocking portion for at least partially obstructing the annular opening, and an end projection at a terminal end of the blocking portion to resist expulsion of the implant through the annular opening. In yet another form, the implant retention device may include an elongate blocking member having annulus connector portions extending from each side of the blocking member for engaging with an annular wall.

15 Claims, 22 Drawing Sheets

U.S. PATENT DOCUMENTS

| | | |
|---|---|---|
| 6,245,107 B1 | 6/2001 | Ferree |
| 6,402,750 B1 | 6/2002 | Atkinson et al. |
| 6,419,704 B1 | 7/2002 | Ferree |
| 6,482,235 B1 | 11/2002 | Lambrecht et al. |
| 6,579,319 B2 | 6/2003 | Goble et al. |
| 6,607,530 B1 | 8/2003 | Carl et al. |
| 6,620,196 B1 | 9/2003 | Trieu |
| 6,669,729 B2 | 12/2003 | Chin |
| 6,733,531 B1 | 5/2004 | Trieu |
| 6,827,743 B2 | 12/2004 | Eisermann et al. |
| 6,878,167 B2 | 4/2005 | Ferree |
| 6,974,479 B2 | 12/2005 | Trieu |
| 7,004,970 B2 | 2/2006 | Cauthen, III et al. |
| 7,033,393 B2 | 4/2006 | Gainor et al. |
| 7,223,289 B2 | 5/2007 | Trieu et al. |
| 7,291,169 B2 | 11/2007 | Hodorek |
| 7,338,525 B2 | 3/2008 | Ferree |
| 7,780,708 B2 | 8/2010 | Morris et al. |
| 2003/0195514 A1 | 10/2003 | Trieu et al. |
| 2003/0204260 A1 | 10/2003 | Ferree |
| 2004/0049283 A1 | 3/2004 | Patel |
| 2004/0088053 A1 | 5/2004 | Serhan et al. |
| 2004/0088054 A1 | 5/2004 | Berry |
| 2004/0111161 A1 | 6/2004 | Trieu |
| 2004/0153078 A1 | 8/2004 | Grinberg |
| 2004/0210310 A1 | 10/2004 | Trieu |
| 2004/0220615 A1 | 11/2004 | Lin et al. |
| 2005/0010293 A1 | 1/2005 | Zucherman |
| 2005/0015150 A1 | 1/2005 | Lee |
| 2005/0113924 A1 | 5/2005 | Buttermann |
| 2005/0125066 A1 | 6/2005 | McAfee |
| 2005/0143740 A1 | 6/2005 | Morris et al. |
| 2005/0143826 A1 | 6/2005 | Zucherman et al. |
| 2005/0159817 A1 | 7/2005 | Ferree |
| 2005/0171604 A1 | 8/2005 | Michalow |
| 2005/0192671 A1 | 9/2005 | Bao et al. |
| 2005/0216087 A1 | 9/2005 | Zucherman et al. |
| 2005/0234460 A1 | 10/2005 | Miller |
| 2005/0261773 A1 | 11/2005 | Ferree |
| 2005/0261774 A1 | 11/2005 | Trieu |
| 2006/0004456 A1* | 1/2006 | McKay .................. 623/17.16 |
| 2006/0084983 A1 | 4/2006 | Kim |
| 2006/0095136 A1 | 5/2006 | McLuen |
| 2006/0190083 A1 | 8/2006 | Arnin et al. |
| 2006/0210594 A1 | 9/2006 | Trieu |
| 2006/0235403 A1 | 10/2006 | Blain |
| 2006/0247665 A1 | 11/2006 | Ferree |
| 2006/0247776 A1 | 11/2006 | Kim |
| 2006/0247784 A1 | 11/2006 | Kim |
| 2006/0247785 A1 | 11/2006 | Gorensek et al. |
| 2006/0253121 A1 | 11/2006 | Gorensek et al. |
| 2006/0253132 A1 | 11/2006 | Evans et al. |
| 2006/0253199 A1 | 11/2006 | Lehuec et al. |
| 2007/0049942 A1 | 3/2007 | Hindrich et al. |
| 2007/0055373 A1 | 3/2007 | Hudgins et al. |
| 2007/0088358 A1 | 4/2007 | Yuan et al. |
| 2007/0118128 A1 | 5/2007 | Light et al. |
| 2007/0135920 A1 | 6/2007 | Ferree |
| 2007/0161991 A1 | 7/2007 | Altarac et al. |
| 2007/0162131 A1 | 7/2007 | Friedman et al. |
| 2007/0191849 A1 | 8/2007 | ElAttrache et al. |
| 2007/0191956 A1 | 8/2007 | Prewett et al. |
| 2007/0191957 A1 | 8/2007 | Anderson et al. |
| 2008/0009943 A1* | 1/2008 | Zarda et al. ............ 623/17.11 |
| 2008/0097611 A1 | 4/2008 | Mastrorio et al. |

FOREIGN PATENT DOCUMENTS

| | | |
|---|---|---|
| WO | 2006065774 | 6/2006 |
| WO | 2007121320 | 10/2007 |

* cited by examiner

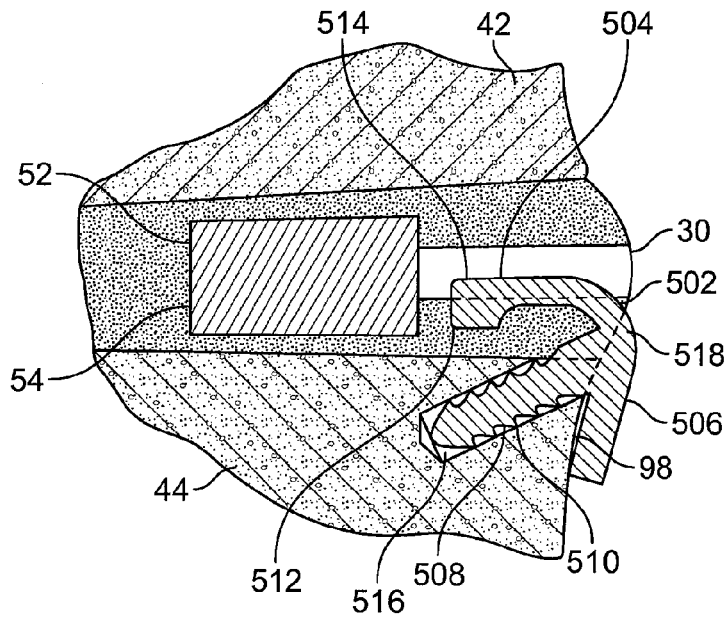
FIG. 14
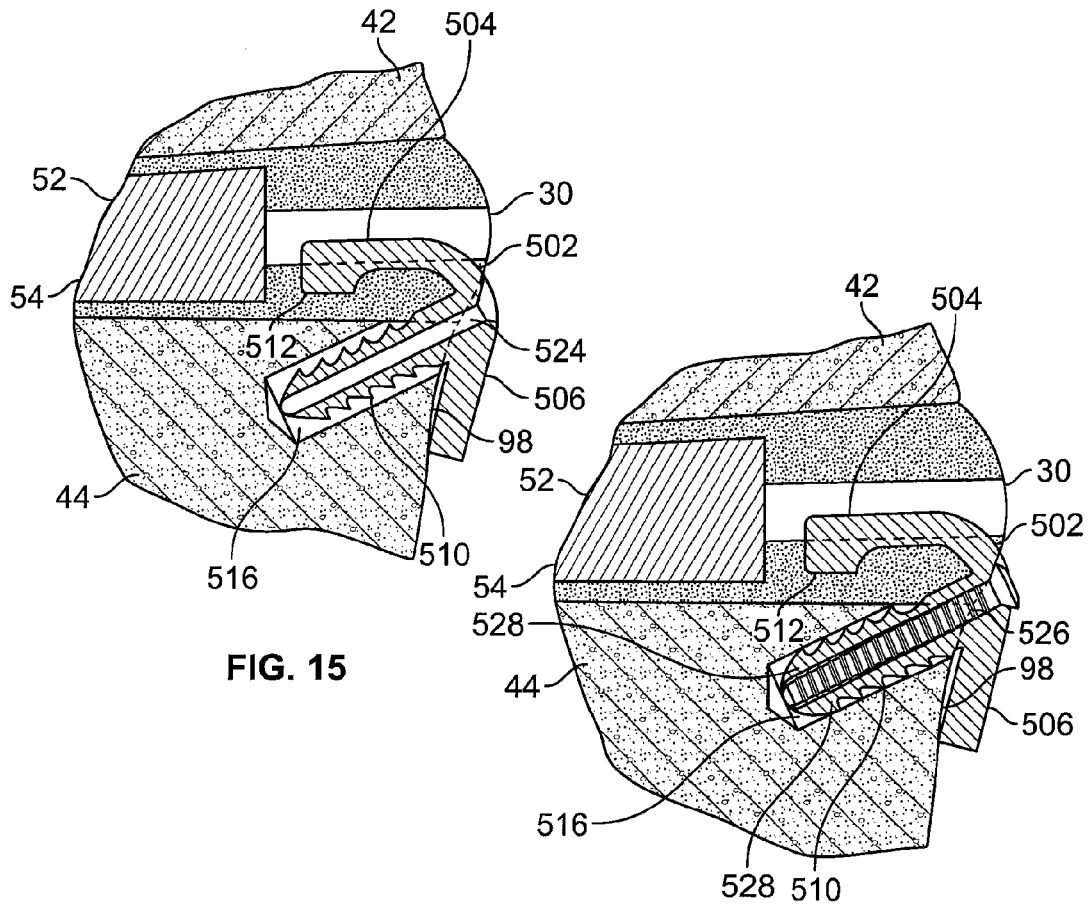
FIG. 15
FIG. 16

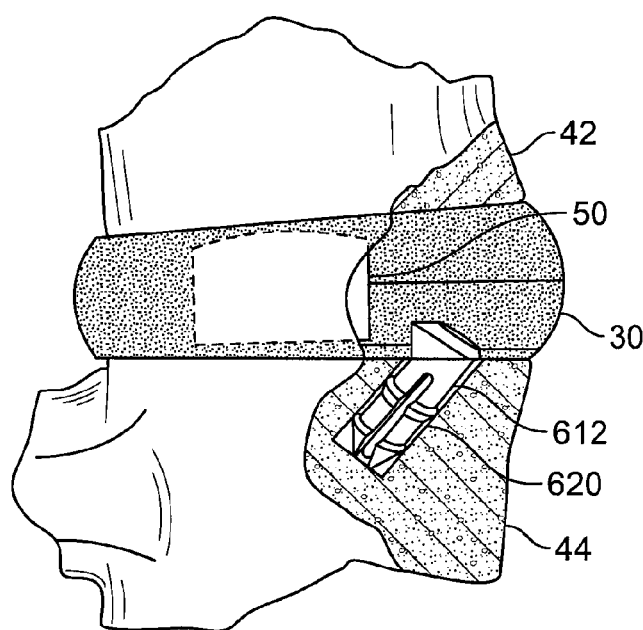
FIG. 41
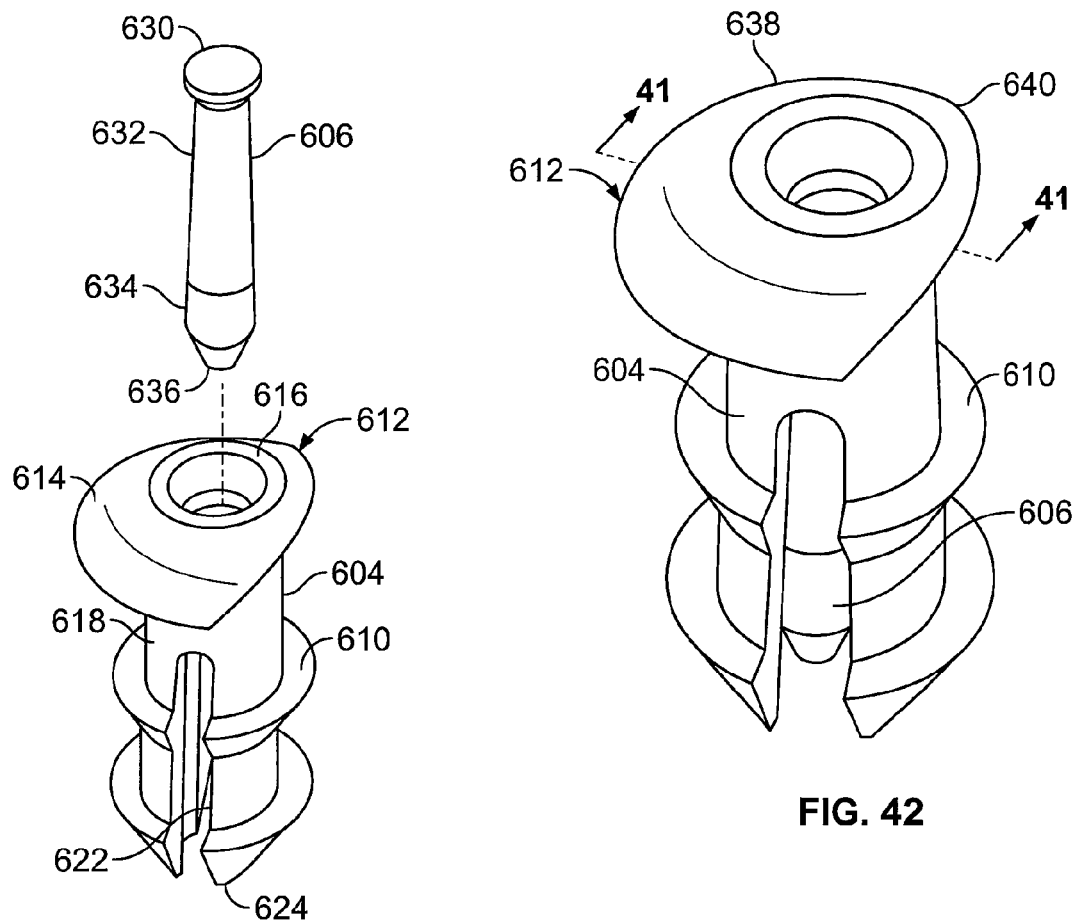
FIG. 42
FIG. 43

IMPLANT RESTRAINT DEVICE AND METHODS

CROSS REFERENCE TO RELATED APPLICATIONS

This application claims the benefit of U.S. Provisional Application No. 60/871,641, filed Dec. 22, 2006, and U.S. Provisional Application No. 60/948,273, filed Jul. 6, 2007, both of which are hereby incorporated by reference as if reproduced herein in their entirety.

FIELD OF THE INVENTION

The invention relates to artificial intervertebral implants and devices for securing and retaining the implant in an intervertebral space.

BACKGROUND OF THE INVENTION

The most common orthopedic condition for which professional medical treatment is sought is lower back pain. Although many factors may be responsible for causing lower back pain, a principal factor is damage or degeneration of an intervertebral spinal disc resulting in impingement on the nerve system, specifically the spinal cord, located within the spine. Such impingement may result in, for instance, loss of mobility, urinary and fecal incontinence, and sciatica or pain experienced in the extremities.

Damage to or degeneration of a spinal disc can result from a number of factors such as abuse or age. The disc itself is composed primarily of an annulus and a nucleus contained therein. The annulus is a fibrous annular piece that attaches to the adjacent vertebrae and contains the nucleus, which is in turn a gel-like viscous material capable of shock absorption and flowable to permit poly-axial rotation and resilient compression of the vertebrae and spine. Most frequently, disc degeneration results from damage occurring to the annulus such that the flowable nucleus material may leak or seep out of the annulus. Disc degeneration also can occur in other ways, such as by being deprived of nutrient flow leading to a dried and susceptible to damage disc. Because the nuclear material is flowable, extensive damage to the annulus is not necessary for leakage to occur.

A recent, though not new, development for spinal surgery is a procedure known as disc arthroplasty for restoring or reconstructing the disc using a prosthesis to replace a portion or entirety of the damaged disc. The primary objective of disc arthroplasty is to restore or maintain the normal disc anatomy and functions, while addressing and treating the causes of the pain.

Two types of prostheses for disc arthroplasty are currently believed to merit further development by medical science and research. One type is a total disc prosthesis, or TDP, where the entire spinal disc is replaced after radial discectomy. A typical TDP includes structures that together mimic the properties of a natural disc.

The other type is a disc nucleus prosthesis, or DNP, that is used to replace only the nucleus of a spinal disc after a nucleotomy while retaining the annulus of the disc and, possibly, the end plates intact. As discussed above, failure of the natural disc does not require extensive damage to the annulus, and the annulus would often be capable of retaining a non-flowing prosthetic nucleus. Implantation of a DNP involves clearing of the natural nucleus from the annulus through the procedure known as nucleotomy, and inserting the DNP within the annulus. Accordingly, disc nuclear prostheses (DNPs) are typically smaller and require less extensive surgery than TDPs do.

An issue related to DNPs is implant extrusion, defined as the tendencies for an implant not to remain seated, and for the implant to back out of its intended seat in the nuclear space. To prevent this, many designs for disc implants attempt to secure to the end plates of the vertebrae by providing securement features on the implant. The nuclear implants frequently have one or more restraining features, such as, for example, keels or other implant protrusions that seat into the bone, apertures integrated into the implant for bone in-growth such as a porous surface or coatings, or screws to screw the implant to the bone. These and other similar features restrain the implant in a predetermined orientation to the surrounding boney bodies to thereby properly support the skeletal structure and prevent damage of any soft tissues. These features, however, may violate the integrity of the end plates to a degree where revision surgery is limited. Violation of the vertebrae by the securement may cause bleeding, or calcification of the end plate, either of which can result in pain, loss of mobility, necrosis, or deterioration of any implant device.

Some arthroplasty devices are designed to float or sit unrestrained within a ligamentous joint capsule. These devices may rely purely on the soft tissue holding the replacement device in the predetermined position. An unrestrained intervertebral artificial nucleus device would benefit from an intact annulus to secure the implant in the predetermined position and prevent its expulsion into the sensitive nerve structure located just outside the annulus. The health of the annulus, however, is often compromised through the degenerative disc disease process and may not be intact. The annulus may have tears or may be poorly nourished and weak such that it cannot adequately serve by itself to restrain the nucleus replacement device within the confines of the annulus. Additionally, the annulus is typically incised during surgery to make an opening for removal of the diseased nucleus material and to serve as a window for placing the nucleus replacement device in its predetermined position. It is possible for this window to serve as an undesired expulsion portal for the nucleus implant.

For these and other reasons, the implant retention devices described herein may be utilized to assist in the retention of a nuclear implant, particularly those that do not have other restraining features, in a predetermined skeletal relationship.

SUMMARY OF THE INVENTION

In accordance with an aspect of the present invention, an implant retention device is provided to assist in restraining movement of a nuclear implant and to assist in limiting expulsion of the nuclear implant through an incision portal or defect in the annular wall. In general, the implant retention device blocks or obstructs at least a portion of an opening in the annular wall, thereby keeping the implant from exiting the nuclear space through the annular opening. By one approach, the implant retention device may comprise a U-shaped member for inserting at least partially into the opening in the annulus. At least one engagement element extends from the U-shaped member, wherein the engagement element is configured for engagement with an exterior surface of at least one of the vertebral bodies. As one illustrative example, a pair of engagement elements extends from the U-shaped member, wherein a first of the pair of engagement elements engages along the exterior surface of the upper vertebral body and a second of the pair of engagement elements engages along the exterior surface of the lower vertebral body. The engagement element may include at least one aperture therethrough for receiving a fastener to secure the engagement element to the exterior surface of the at least one vertebral body. Further, the engagement element may include a contoured surface for improved engagement with the vertebral body. The U-shaped member and the engagement element may be comprised of resilient material to allow for relative movement between the upper and lower vertebral bodies. Further, the U-shaped member may include at least one barb projecting therefrom to assist in securing the implant retention device in place. The U-shaped member may include a contact member extending therefrom to restrict movement of the implant toward the annular opening. The U-shaped member may include a center portion and a pair of prongs extending therefrom. The engagement element may extend generally transverse from at least one of the prongs. By one approach, the center portion and a portion of the prongs are inserted in the annular opening. Alternatively, a portion of one of the pair of prongs may be inserted in the annular opening and a portion of the other of the pair of prongs engages with the vertebral body, with the center portion extending between the prongs. The engagement element may comprise a fastener extending into the vertebral body. In addition, the engagement element may include a corner portion for fitting about a corner portion of the vertebral body.

In a further embodiment, an implant restraint device for a nuclear implant is provided, the device comprising a mounting portion to be positioned adjacent one of upper and lower adjacent vertebral bodies. A blocking portion for at least partially obstructing the annular opening extends from the mounting portion. In addition, an enlarged end projection of the blocking portion is inserted through the opening and sized to resist expulsion of the blocking portion through the annular opening. The retention device may include a neck portion between the mounting portion and the blocking portion configured to extend through a portion of the annular window. The neck portion has a raised interior contour between the blocking portion and the mounting portion to space the device from an edge of the annular opening to avoid contact with the annular wall. In one form, the enlarged end projection extends more proximately to the endplate than the neck portion. Preferably, at least one fastener extends from the mounting portion for securing the mounting portion to the vertebral body. The fastener may extend from any point along the length of the mounting portion, such as, for example, from the distal end or a point of intersection of the blocking portion and the mounting portion. The fastener may extend at a 45 or 90 degree angle to the mounting portion, although other angles are contemplated. By one optional approach, the fastener may be a discrete fastener and the mounting portion may include an aperture sized to receive the discrete fastener. Alternatively, the fastener may be integrally formed with the mounting portion. The integral fastener may include a plurality of concentric ridges configured to be press fit into a preformed opening in the vertebral body. The integral fastener may optionally be hollow and split to accommodate an extension member therein to secure the fastener in a preformed opening in the vertebral body.

By another approach, the implant retention device may comprise an elongated lateral blocking member for inserting at least partially into the nuclear space to obstruct the opening in the annular wall. The implant retention device has annulus connector portions extending from each side of the blocking member for engaging with a surface of the annular wall. In one form, the connector portions include integral S-shaped hooking portions extending from each end of the blocking member to engage with an exterior surface of the annular wall. The device is configured to transition between a compressed position wherein the elongated member and S-shaped hooking portions extending therefrom have a compressed span less than the annular wall opening for insertion through the opening and an expanded position wherein the elongated member and S-shaped hooking portions extending therefrom have an expanded span greater than the annular wall opening for obstructing the opening. The compressed position may be formed by folding ends of the elongated lateral blocking member inwardly along a centerline thereof. The implant retention device may then be inserted into the annular opening such that the elongated blocking member is positioned between the nuclear implant and the annular opening and portions of the retention members are engaged with an exterior surface of the annular wall. The device may further include a retraction portion, such as a central protrusion in the elongated lateral blocking member extending between the annulus connector portions, to facilitate removal of the elongated lateral blocking member from the nuclear space. After insertion of the implant retention device, a portion of the retraction member extends from the annular opening. The implant retention device may then be removed by grasping the portion of the retraction member extending from the annular opening and pulling the implant retention device through the annular opening.

In a further embodiment, the implant retention device comprises a flexible shield having a compressed position with a span less than the opening in the annular wall and an expanded position with a span greater than the opening in the annular wall. The flexible shield is unattached to the annular wall and configured to obstruct the annular opening within the nuclear space and retain an implant within the nuclear space. The flexible shield may have a center annular portion and wing portions extending laterally from opposing sides of the center portion. The flexible shield has a compressed position with a span less than the opening in the annular wall and an expanded position with a span greater than the opening in the annular wall with the implant inserted through the annular wall opening to keep the implant in the nuclear space. The shield is positioned adjacent a trailing end of the implant, between the implant and the annular opening. The center circular portion of the shield may optionally have an aperture therethrough to facilitate compression of the shield, such that the aperture is reduced in size with resilient shifting of the wing portions to a compressed position thereof. The wing portions are folded inwardly to reduce the lateral span of the flexible shield, wherein the folding in of the wing portions also reduces the diameter of the center portion such that the flexible shield is compressed to fit through the annular opening. The diameter of the center portion is preferably greater than the height of the implant. In addition, the flexible shield may have an arcuate shape with a concave face for conforming with a similarly shaped implant.

In accordance with another aspect, a method is provided wherein an annular opening is formed in the annular wall by cutting the annular wall for insertion of a nuclear implant into a nuclear space. An implant retention device is shifted into a compressed position such that the implant retention device has a compressed size less than the size of the annular opening for insertion of the device through the annular opening. The implant retention device is then inserted through the annular opening in the compressed position, such that the implant retention device is positioned between the nuclear implant and the annular opening and is spaced from the annular wall. The implant retention device is then shifted to an expanded position such that the implant retention device has an expanded size greater than the size of the annular opening.

The implant retention device may be separate from the implant, such as a flexible shield positioned adjacent a trailing end of the implant between the implant and the annular opening, wherein the compressed position is formed by compressing together end portions of the shield.

In another embodiment, an expulsion limiting device is provided to be used with a nuclear implant. A blocking member is engaged with an interior surface of one of the vertebral bodies and is positioned such that at least a portion of the blocking member obstructs the annular opening to interfere with movement of the implant out of the nuclear space. When a two-part articulating implant having articulation surfaces between the parts is implemented, the portion of the blocking member obstructing the annular opening is preferably aligned with only one part of the two-part implant to allow for relative movement and articulation between each part of the two-part implant. The blocking member may include a bumper having a blocking portion configured to at least partially obstruct the annular opening and a fastener for coupling the bumper to one of the vertebral bodies. In another form, the blocking member has a first fastening portion for engaging with a vertebral endplate and a second fastening portion for engaging with another portion of a vertebral body. Optionally, the blocking member may include a pair of bodies movably connected to one another, with a fastening portion of each body for engaging one of the vertebral bodies. The fastening portion may be configured for penetrating a vertebral body. In addition, the movable connection between the pair of bodies may include a biasing member to bias the fastening portion of each body toward a compressed orientation, wherein the fastening portions are urged toward one another.

In another form, the blocking member generally comprises a head portion and a shaft portion. The head portion and the shaft portion may optionally mate in an angled configuration may have a separate bumper member, such as a washer. The shaft portion may optionally be threaded to drive the shaft portion into the vertebral body or the shaft portion may have a plurality of concentric ridges configured to be press fit into a preformed opening in the vertebral body. The shaft portion may comprise at least one helical prong extending from the head portion. In addition, the shaft portion may include an enlarged tip portion to secure the blocking member in the vertebral body. By one optional approach, the blocking member may be hollowed and split to accommodate an insertion member therein to secure the blocking member in the vertebral body. The insertion member may optionally include barbs that are configured to deploy radially to limit rotation of the blocking member. The insertion member may comprise a shaft having a widened base portion that operates to splay apart the split blocking member to secure the blocking member in the vertebral body.

BRIEF DESCRIPTION OF THE DRAWINGS

FIG. 14 is a partial cross-sectional side view of the implant retention device and spinal section of FIG. 13 taken along line 14-14 thereof;

FIG. 15 is a cross-sectional side view of a sixth embodiment of an implant retention device showing the implant retention device mounted to a vertebra of a spinal section and inserted in an annular opening, with a nuclear implant inserted in a nuclear space of the spinal section;

FIG. 16 is a cross-sectional side view of the implant retention device and spinal section of FIG. 15 showing an expansion member inserted therein;

FIG. 41 is a partial cross-sectional side view of the spinal section of FIG. 40 showing the implant retention device and nuclear implant;

FIG. 42 is a perspective view of the implant retention device of FIG. 40;

FIG. 43 is an exploded perspective view of the implant retention device of FIG. 42;

DETAILED DESCRIPTION

Figure 1:
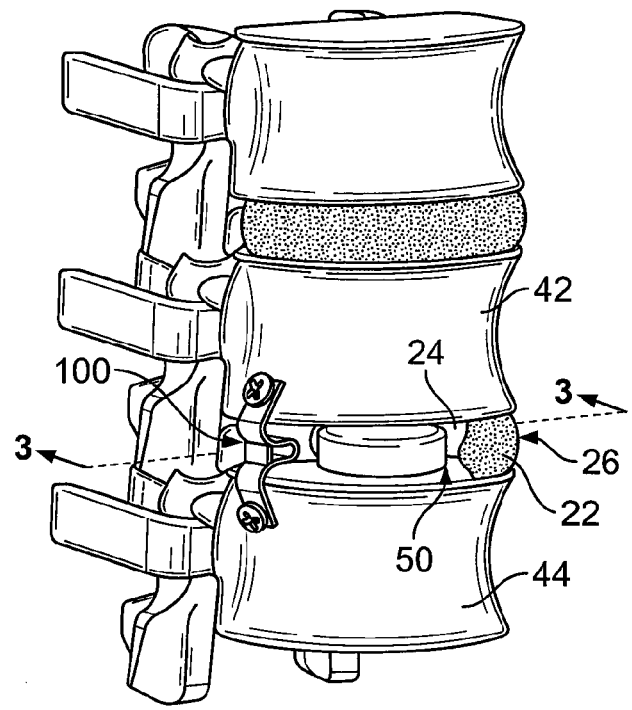
FIG. 1 is a perspective view of a first embodiment of an implant retention device showing the implant retention device mounted to adjacent vertebra of a spinal section and inserted in an annular opening, with a nuclear implant inserted in a nuclear space of the spinal section.
Figure 2:
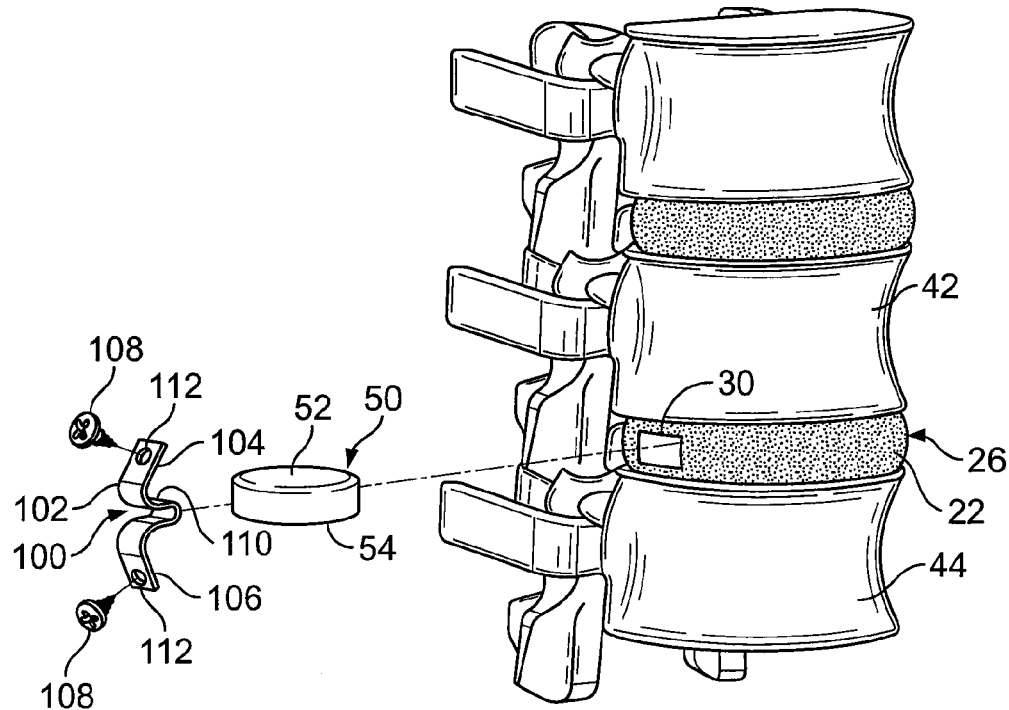
FIG. 2 is an exploded perspective view of the implant retention device and the spinal section of FIG. 1.
Figure 3:
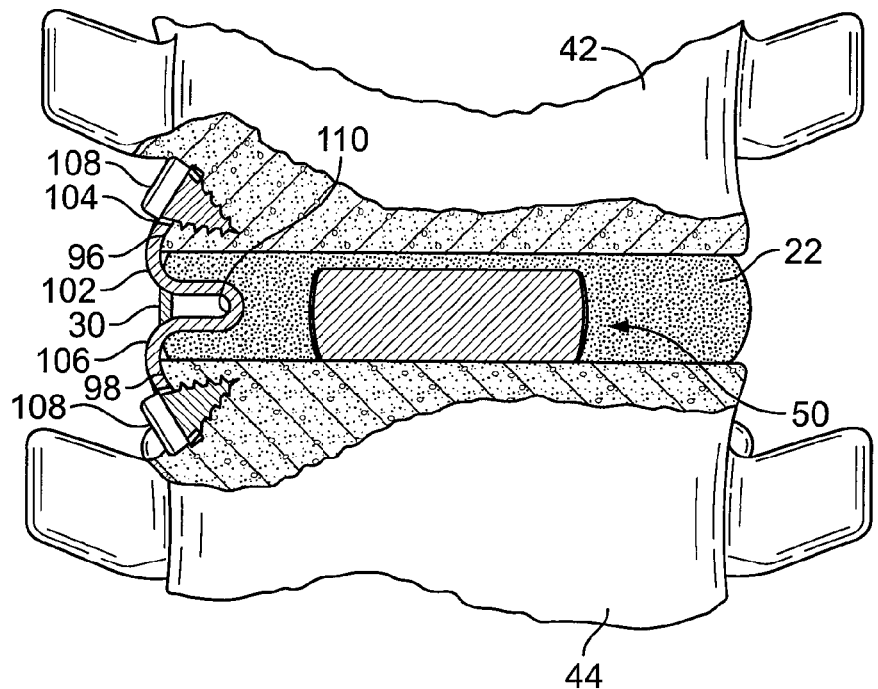
FIG. 3 is a partial cross-sectional front view of the implant retention device and spinal section of FIG. 1 taken along line 3-3 thereof.

Generally speaking, pursuant to these various embodiments, implant retention devices are disclosed herein, with each device directed to maintaining a nuclear implant in position within a nuclear space and limiting the implant from backing out through an opening in the annulus. It shall be understood that retention refers to retaining, restraining, controlling, or maintaining the implant within the nuclear space to limit the expulsion of the implant out of the nuclear space through the annular opening. Referring now to the drawings, and in particular to FIGS. 1-3, a first embodiment of an implant retention device 100 is shown. A nuclear implant 50 is inserted through an annular opening 30 in the wall of the annulus 22 and positioned within a nuclear space 24 of a disc 26 located between adjacent upper vertebra 42 and lower vertebra 44. The annular opening 30 is typically created during surgery prior to implantation of the nuclear implant 50 to serve as a portal for removing the nucleus and as a surgical window for inserting the implant 50 into the nuclear space 24. However, the annular opening 30 can also be formed from a tear or weakening of the annulus 22. The annular opening 30 generally extends from the exterior of the annulus 22 through to the nuclear space 24.

The implant retention device, for this and other implant retention device embodiments disclosed herein, is generally shown being used in conjunction with a block-shaped nuclear implant 50 having a top portion 52 and a bottom portion 54. Each portion 52, 54 has a peripheral shape of an oval or racetrack shape, having a greater longitudinal dimension than a lateral dimension. Alternatively, the implant may be a two-piece articulating implant, with a concave recess formed in the top portion and a corresponding dome surface formed in the bottom portion, with the dome surface being received in the concave recess to allow for relative translational motion and movement between the top portion and the bottom portion. The nuclear implant 50 shown and described herein is used as an illustrative example, with other configurations of nuclear implants or nuclear replacement devices being contemplated for use in conjunction with the implant retention devices discussed herein.

The implant retention device 100 is comprised of a flexible member 102 secured to the adjacent upper vertebra 42 and lower vertebra 44. The flexible member 102 includes a generally U-shaped center protrusion 110 that is inserted into the annular opening 30 to block expulsion of the nuclear implant 50. The center protrusion 110 has a height and width sized to at least partially obstruct the annular opening 30. The flexible member 102 further comprises an upper extension 104 and a lower extension 106 extending at an angle from each end of the U-shaped center protrusion 110, such that when the center protrusion 110 is inserted in the annular opening 30, at least a portion of the upper extension 104 is seated flush against a portion of an exterior surface 96 of the upper vertebra 42 and at least a portion of the lower extension 106 is seated flush against a portion of an exterior surface 98 of the lower vertebra 44. Each of the upper extension 104 and the lower extension 106 includes an aperture 112 therethrough. A fastener 108, such as, for example, a bone screw, is inserted through the aperture 112 of each of the lower extension 106 and upper extension 104 and is driven into the vertebral bodies 42, 44 to anchor the flexible member 102 to the vertebral bodies 42, 44 and secure the flexible member 102 in place. The implant retention device 100 is externally secured to the vertebral bodies 42, 44, thus providing for ease of installation of the device. When the implant retention device 100 is mounted to the upper vertebra 42 and the lower vertebra 44, the device 100 acts as a plug to at least partially fill the annular opening 30 and block the exit path of the nuclear implant 50 to prevent the expulsion of the implant 50 from the nuclear space 24. Modification or customization of the nuclear implant 50 is not required to accommodate this implant retention device.

The series of bends forming the center protrusion 110 and upper 104 and lower 106 extensions, in conjunction with the material, provides resiliency to the flexible member 102. The flexible nature of the flexible member 102 allows for relative movement of the upper vertebra 42 and the lower vertebra 44, with the flexible member 102 configured to flex, compress, and expand to accommodate movement of the adjacent vertebral bodies 42, 44, such that the range of relative motion of the vertebral bodies 42, 44 is not greatly compromised by the installation of the device 100. The flexible member 102 is made of a resilient material, such as, for example, a polymer or a resilient metal, such as, for example, Nitinol. Further, the flexible member 102 may be formed, for example, from a flexible solid or a flexible mesh. By another approach, the flexible member 102 may be hinged or may include a stiffer portion, made of metal, for example, and a flexible portion made of a biocompatible interwoven fabric, such as, for example, GORE-TEX® or a polyethylene mesh.

Figure 4:
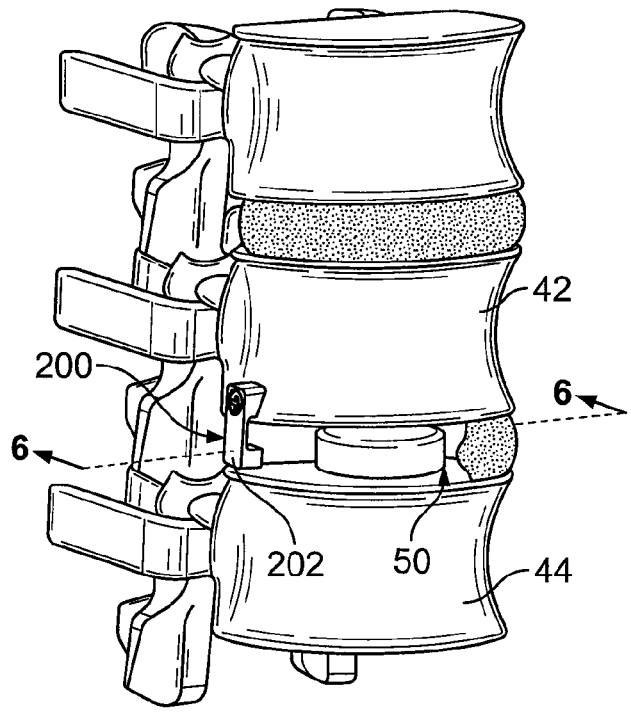
FIG. 4 is a perspective view of a second embodiment of an implant retention device showing the implant retention device mounted to a vertebra of a spinal section and inserted in an annular opening, with a nuclear implant inserted in a nuclear space of the spinal section.
Figure 5:
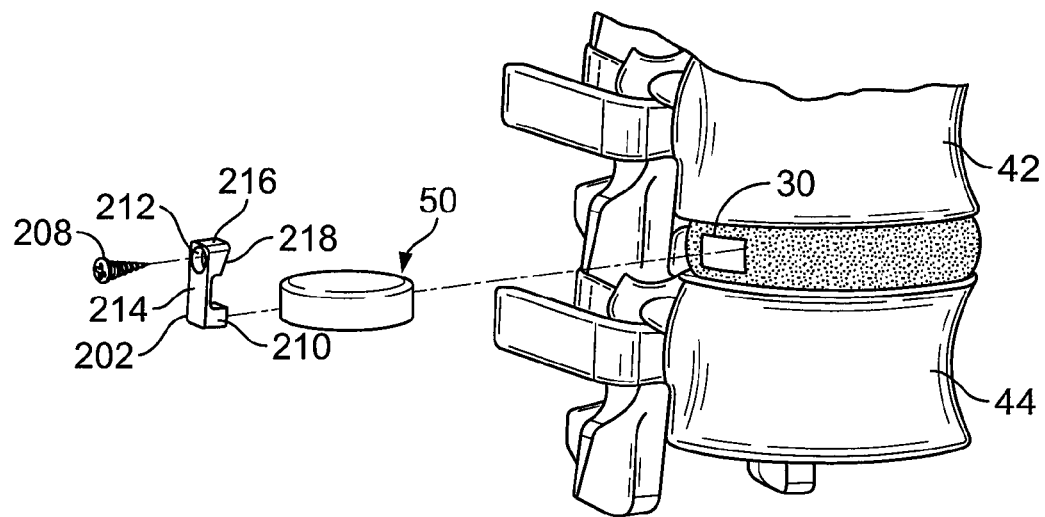
FIG. 5 is an exploded perspective view of the implant retention device and the spinal section of FIG. 4.
Figure 6:
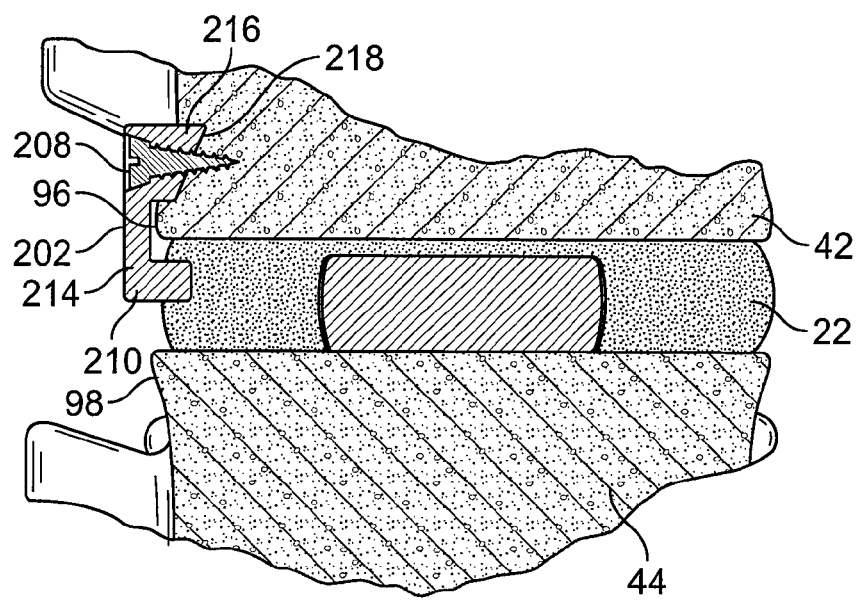
FIG. 6 is a partial cross-sectional front view of the implant retention device and spinal section of FIG. 4 taken along line 6-6 thereof.

Referring now to FIGS. 4-6, a second embodiment of an implant retention device 200 is shown. The retention device 200 is comprised of a generally U-shaped rigid blocking member 202. The U-shaped blocking member 202 is preferably manufactured of a polymer or titanium, but may be made of any other known metals, ceramic, plastic, composite material, or elastomer. The U-shaped blocking member 202 includes a center linear portion 214 connecting an upper extension 216 for mounting to the upper vertebral body 42 and a lower extension 210 that is inserted in the annular opening 30. The lower extension 210 and the upper extension 216 preferably extend generally transversely from the linear portion 214, such that the extensions 210, 216 are generally parallel in a U-shaped configuration.

A face portion 218 of the upper extension 216 is positioned adjacent the upper vertebral body 42 and seated flush against the exterior surface 96 of the upper vertebral body 42. The face portion 218 may be contoured or angled for improved mating between the face portion 218 and the upper vertebral body 42. As an illustrative example, and as shown in FIGS. 4-6, the face portion 218 has an inclined orientation for improved mating with the exterior surface of the upper vertebral body 42. By one approach, the face portion 218 may include, for example, teeth or other protrusions to assist in maintaining the implant retention device in its predetermined location. The upper extension 216 includes an aperture 212 therethrough. A fastener 208 is inserted through the aperture 212 and driven into the upper vertebral body 42 to engage with the upper vertebral body 42 to secure the rigid blocking member 202 to the upper vertebral body 42. The fastener 208 may include, for example, a threaded bone screw or any other suitable fastener as known in the art.

The lower extension 210 is sized to at least partially extend into the annular opening 30. The length of the lower extension 210 may be varied such that, for example, the lower extension 210 may extend fully through the annular opening 30 and into the nuclear space 24 or may just cover the annular opening 30 without extending therein. Further, the lower extension 210 is sized to at least partially obstruct the annular opening 30 to block expulsion of the nuclear implant 50. The lower extension 210 is preferably smooth or otherwise formed so as to not damage or interrupt the articulating motion of the implant 50. As the rigid blocking member 202 is only attached to one vertebral body, the rigid blocking member 202 does not limit motion between the vertebral bodies 42, 44, thereby allowing for relative movement between vertebral bodies 42, 44. Although the blocking member 202 is shown mounted to the upper vertebral body 42, it should be noted that the blocking member 202 may be mounted to the lower vertebral body 44, with the upper extension 216 being secured to the exterior surface 98 of the lower vertebral body 44 by the fastener 208. Again, this embodiment does not require any modification or customization of the nuclear implant 50 to accommodate the implant retention device 200. The implant retention device 200 is externally secured to the vertebral body, thus providing for ease of installation of the device.

Figure 7:
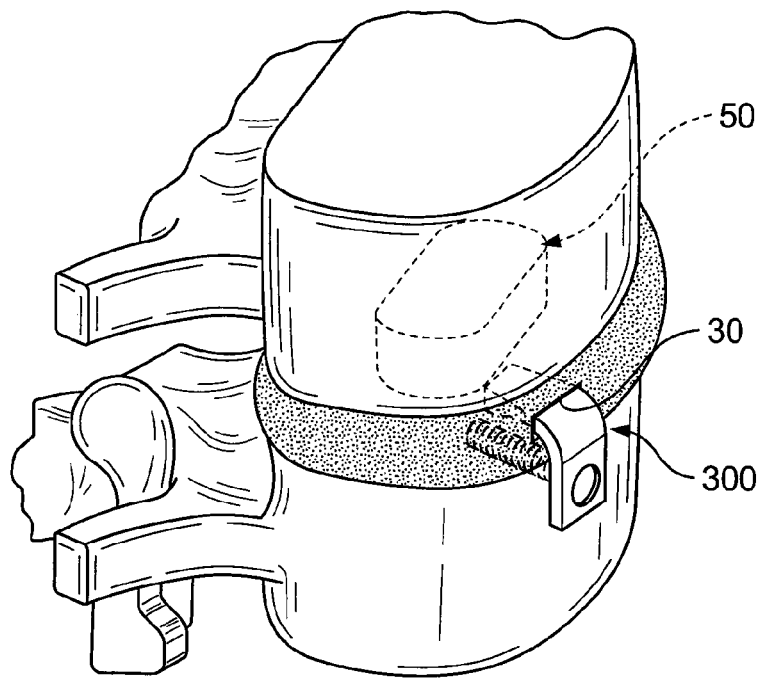
FIG. 7 is a first perspective view of a third embodiment of an implant retention device showing the implant retention device mounted to a vertebra of a spinal section and inserted in an annular opening, with a nuclear implant inserted in a nuclear space of the spinal section.
Figure 8:
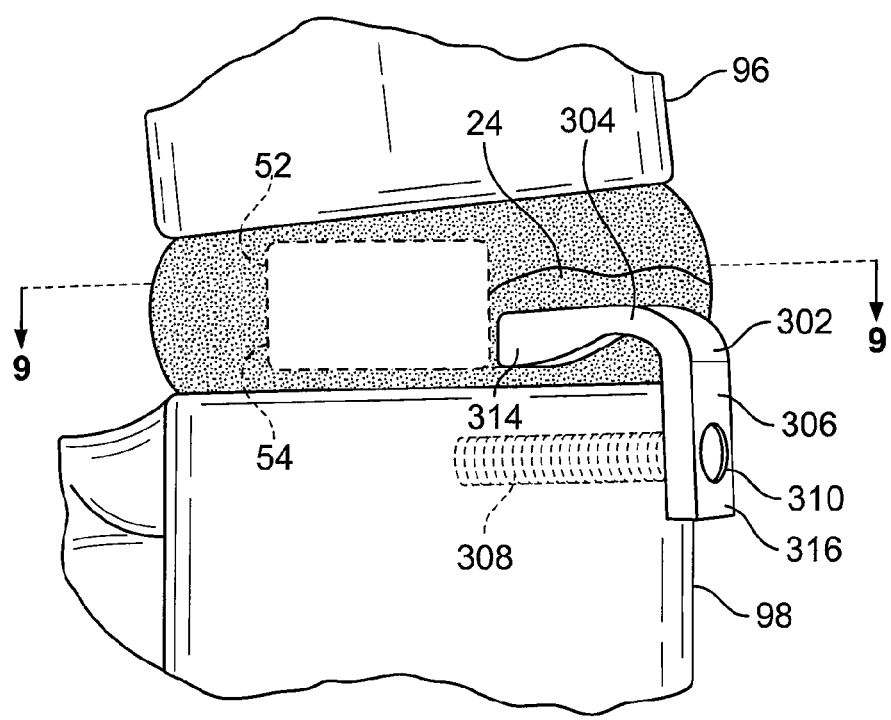
FIG. 8 is a second perspective view of the implant retention device of the implant retention device and spinal section of FIG. 7 showing the implant retention mounted to a vertebra and inserted in the annular opening.
Figure 9:
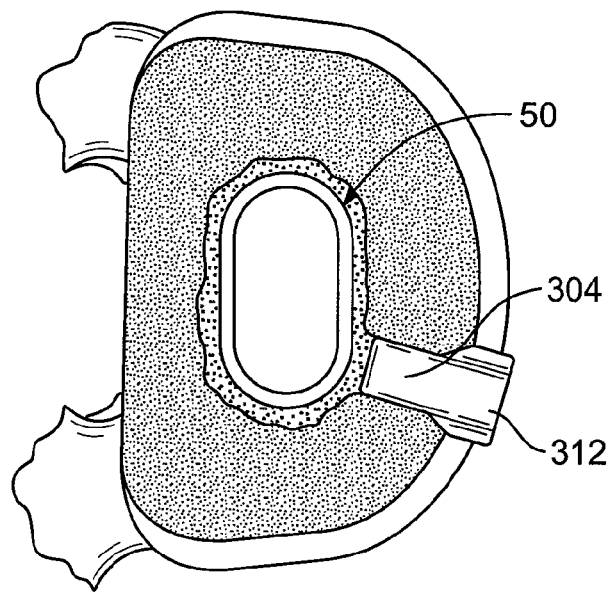
FIG. 9 is a cross-sectional top view of the spinal section of FIG. 8 taken along line 9-9 thereof and showing the implant retention device and nuclear implant.

Referring now to FIGS. 7-9, an alternative embodiment of an implant retention device is shown. The implant retention device 300 is comprised of a generally V-shaped rigid blocking member 302 having a mounting portion 306 and a blocking portion 304. The V-shaped rigid blocking member 302 is preferably manufactured of a polymer or titanium, but may be made of any other known metals, ceramic, plastic, composite material, or elastomer. At least a portion of the blocking portion 304 is inserted in the annular opening 30, such that the annular opening 30 is at least partially obstructed to prevent expulsion of the implant 50 through the annular opening 30. The blocking portion 304 is preferably wider at the proximal end 312 adjacent the point of intersection with the mounting portion 306, such that the proximal end 312 of the blocking portion 304 preferably fully obstructs the annular opening 30. In addition, the blocking portion 304 is preferably thicker or has a projection at a distal end 314 thereof, and becomes thinner or tapers as it approaches the point of intersection with the mounting portion 306, as shown in FIG. 8. The thicker distal end portion 314 is preferably sized such that there is minimal clearance between the distal end 314 and the sidewalls of the annular opening 30 as the distal end 314 is inserted and press fit through the opening 30. Once inserted, the thicker distal end portion 314 further facilitates backout protection, as the thicker distal end 314 will resist being withdrawn from the nuclear space 24 through the annular opening 30. Any force exerted on the thicker distal end 314 of the blocking portion 304 by the implant 50 within the nuclear space 24 will generally not be great enough to expel the thicker distal end 314 back through the annular opening 30.

The blocking portion 304 extends at least partially into the nuclear space 24 and is generally aligned with the bottom portion 54 of the nuclear implant 50. If the nuclear implant 50 moves toward the annular opening 30, the blocking portion 304 will make contact with the bottom portion 54 of the implant 50 to prevent the implant 50 from backing out of the nuclear space 24. It should be noted that the blocking portion 304 may alternatively be aligned with the top portion 52 of the implant 50. This configuration is advantageous for use with articulating two-piece implants, because the blocking portion 304 is aligned to make contact with only one of the implant portions, such that the blocking portion 304 does not interfere with the articulating movement of the implant portions.

As shown, when the blocking portion 304 is inserted through the annular opening 30, at least a portion of the mounting portion 306 is positioned generally adjacent the lower vertebral body 44 and is seated flush against a portion of the exterior surface 98 of the lower vertebral body 44. The angle between the mounting portion 306 and the blocking portion 304 is sized such that the mounting portion 306 is preferably seated flush against the vertebral body 44 when the blocking portion is inserted in the annular opening 30. Alternatively, the mounting portion 306 may be positioned adjacent the exterior surface 96 of the upper vertebral body 42. The mounting portion 306 may be angled or countered to provide improved mating between the mounting portion 306 and the exterior surface 96 of the lower vertebral body 44. By one approach, the surface of the mounting portion 306 adjacent the exterior surface 98 of the lower vertebral body 44 may have projections, teeth, or other protrusions to assist in maintaining the implant retention device 300 in its predetermined position. The mounting portion 306 preferably includes a mounting aperture 310 through the distal end 316 thereof. Alternatively, the aperture 310 may be located anywhere along the length of the mounting portion 306. A fastener 308 is inserted through the aperture 310 and is driven into the lower vertebral body 44 to secure the mounting portion 306 of the rigid member 302 to the lower vertebral body 44, with the mounting portion 306 seated flush against at least a portion of the exterior surface 98 of the lower vertebral body 44. As shown in FIG. 8, the fastener 308 is inserted into the lower vertebral body 44 generally transverse to the mounting portion 306 and generally parallel to the blocking portion 304. Alternatively, the fastener 308 may be inserted through the aperture 310 and into the vertebral body 44 at an angle, with the aperture 310 optionally being contoured or angled to facilitate the angled position of the fastener 308. The fastener 308 may comprise, for example, a threaded bone screw or any other securing member known in the art. Again, as the rigid blocking member 302 is only attached to one vertebral body, the rigid blocking member 302 does not limit motion between the vertebral bodies 42, 44, thereby allowing relative movement between vertebral bodies 42, 44. This embodiment does not require any modification or customization of the nuclear implant 50 to accommodate the implant retention device 300. The implant retention device 300 is externally secured to the vertebral body, thus providing for ease of installation of the device.

Figure 10:
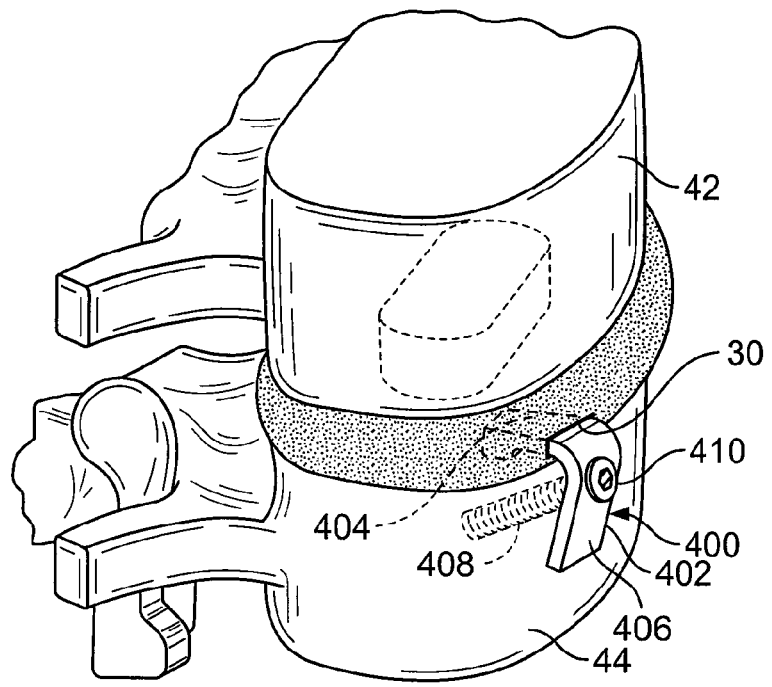
FIG. 10 is a perspective view of a fourth embodiment of an implant retention device showing the implant retention device mounted to a vertebra of a spinal section and inserted in an annular opening, with a nuclear implant inserted in a nuclear space of the spinal section.
Figure 11:
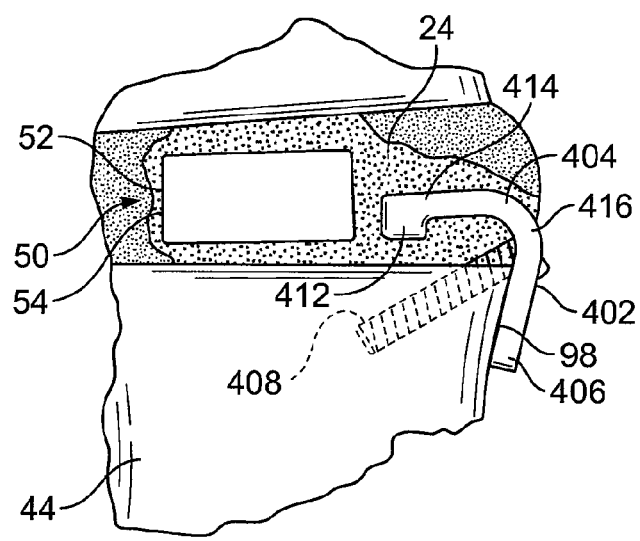
FIG. 11 is a partial side view of the spinal section of FIG. 10 showing the implant retention device and nuclear implant.

Referring now to FIGS. 10-11, an alternative embodiment of an implant retention device 400 is shown. The implant retention device 400 is comprised of a generally V-shaped rigid member 402 having a blocking portion 404 and a mounting portion 406. The V-shaped rigid blocking member 402 is preferably manufactured of a polymer or titanium, but may be made of any other known metals, ceramic, plastic, composite material, or elastomer. As with the implant retention device 300, the blocking portion 404 is inserted in the annular opening 30, such that the annular opening 30 is at least partially obstructed to prevent expulsion of the implant 50 through the annular opening 30. The blocking portion 404 extends at least partially into the nuclear space 24 and is generally aligned with the bottom portion 54 of the implant 50. Alternatively, the mounting portion 406 may be positioned adjacent the upper vertebral body 42, with the blocking portion 404 generally aligned with the top portion 52 of the nuclear implant 50. As with the implant retention device 300, this configuration is advantageous for use with articulating two-piece implants, because the blocking portion 304 is aligned to make contact with only one of the implant portions, such that the blocking portion does not interfere with the articulating movement of the implant portions. The blocking portion 404 has a projection 412 at a distal end 414 thereof, such that the distal end 414 of the blocking portion 404 is thicker than the remainder of the blocking portion 404. The distal end 414, including the projection 412, is sized to fit through the annular opening 30 with minimal clearance. The projection 412 assists in limiting the ability of the implant retention device 400 to back out of the nuclear space 24 through the annular opening 30 as the implant 50 is not likely to exert a force on the blocking portion 404 that is great enough to expel the projection 412 back through the annular opening 30. In addition, the projection 412 on the blocking portion 404 may also catch on a lower edge of the annular opening 30 to resist expulsion of the blocking portion 404 from the nuclear space 24 through the annular opening 30. The blocking portion 404 widens as it approaches the point of intersection with the mounting portion 406 to preferably fully obstruct the annular opening 30.

When the blocking portion 404 is inserted in the annular opening 30, a portion of the mounting portion 406 is positioned generally adjacent the lower vertebral body 44 and seated flush against a portion of the exterior surface 98 of the lower vertebral body 44. The mounting portion 406 has an aperture 410 therethrough, with the aperture 410 preferably located generally adjacent the center point 416 of the V-shaped member 402 where the mounting portion 406 and blocking portion 404 intersect. Alternatively, the aperture may be located anywhere along the length of the mounting portion 406. The aperture 410 is generally sized to receive a fastener 408, such as a threaded bone screw or other fastener known in the art, with the fastener 408 being inserted into the lower vertebral body 44 to secure the rigid member 402 in position, with the mounting portion in generally flush mating contact with the exterior surface 98 of the lower vertebral body 44. The fastener 408 may also penetrate a portion of the annulus 22. The fastener 408 is preferably inserted into the lower vertebral body 44 at a generally 45 degree angle, although other mounting angles may be contemplated. The aperture 410 may optionally be contoured or angled to facilitate the angled position of the fastener 408. Again, as the rigid blocking member 402 is only attached to one vertebral body, the rigid blocking member 402 does not limit motion between the vertebral bodies 42, 44, thereby allowing relative movement between vertebral bodies 42, 44. In addition, this embodiment does not require any modification or customization of the nuclear implant 50 to accommodate the implant retention device 400. The implant retention device 400 is externally secured to the vertebral body, thus providing for ease of installation of the device.

Figure 12:
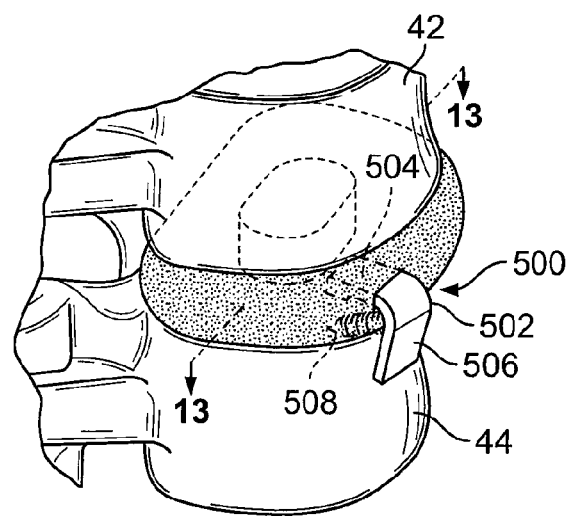
FIG. 12 is a perspective view of a fifth embodiment of an implant retention device showing the implant retention device mounted to a vertebra of a spinal section and inserted in an annular opening, with a nuclear implant inserted in a nuclear space of the spinal section.
Figure 13:
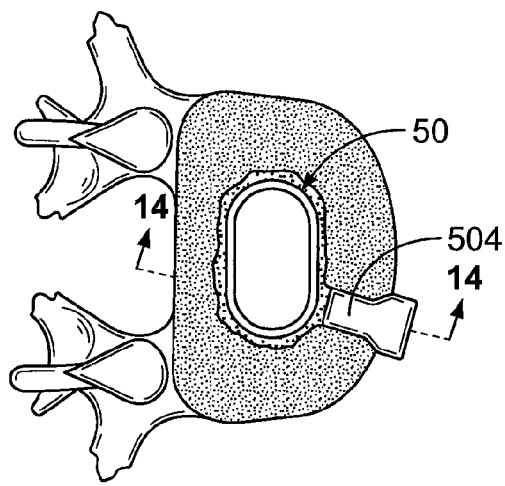
FIG. 13 is a partial cross-sectional top view of the spinal section of FIG. 12 taken along line 13-13 thereof and showing the implant retention device and nuclear implant.

By another optional approach, an additional embodiment of an implant retention device 500 comprises a V-shaped rigid member having an integral fastener. As shown in FIGS. 12-14, the V-shaped rigid member 502 has a blocking portion 504 and a mounting portion 506 having the same general configuration and mounted orientation as the blocking portion 404 and mounting portion 406 of the implant retention device 400, as described above. In addition, the blocking portion 504 also includes a projection 512 extending from a terminal end of the blocking portion 504, wherein the projection 512 will catch on a lower edge of the annular opening 30 to resist expulsion of the blocking portion 404 from the nuclear space 24 through the annular opening 30. The fastener 508 of this device 500 is formed integral with the rigid member 502. The integral fastener 508 extends from an upper end 518 of the mounting portion 506 at a generally 45 degree angle, although other extension angles are contemplated. The fastener 508 includes a plurality of concentric ridges 510 to allow for a press fit insertion into the lower vertebral body 44. A mounting hole 516 may be pre-drilled in the lower vertebral body 44 and, if necessary, through a portion of the annulus 22, with the fastener 508 being pressed into the mounting hole 516.

In addition, and referring now to FIGS. 15-16, the fastener 508 may optionally be hollow and configured to split to allow insertion of an expansion mechanism 526, such as a screw, bolt, or other expansion member. The fastener 508 has a hole 524 through a length thereof, with the hole 524 sized to accommodate an expansion mechanism 526. When the expansion mechanism 526 is inserted into the hollow of the fastener 508, the split sides of the fastener 508 project outwardly and the ridges 510 engage with the side walls of the mounting hole 516 to resist removal from the mounting hole 516. The ends 528 of the split fastener 508 may be compressed together to provide some clearance as the integral fastener 508 is inserted into the mounting hole 516.

The plurality of ridges 510 provide resistance such that the rigid member 502 will remain secured in position. The ridges 510 of the integral fastener 508 are generally more resistant to expulsion from the mounting hole due to vibration as compared to, for example, a screw. In addition, because the fastener 508 is integral with the rigid member 502, the implant retention device 500 is a single piece. As a result, the entire implant retention device 500 would have to be dislodged from its mounted position in order for the nuclear implant 50 to back out of the nuclear space 24. The V-shaped rigid blocking member 502 and integral fastener 508 are preferably manufactured of a polymer or titanium, but may be made of any other known metals, ceramic, plastic, composite material, or elastomer.

Figure 17:
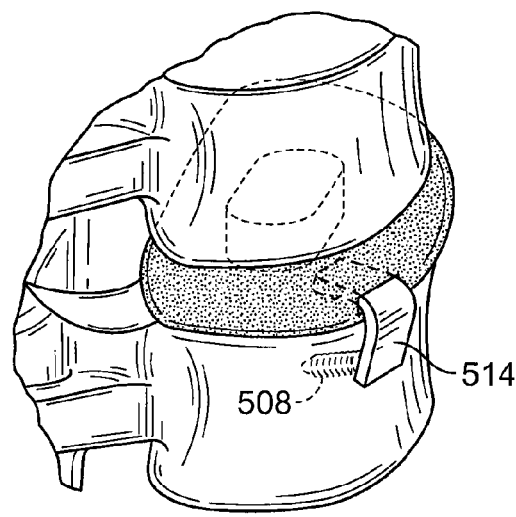
FIG. 17 is a perspective view of a seventh embodiment of an implant retention device showing the implant retention device mounted to a vertebra of a spinal section and inserted in an annular opening, with a nuclear implant inserted in a nuclear space of the spinal section.
Figure 18:
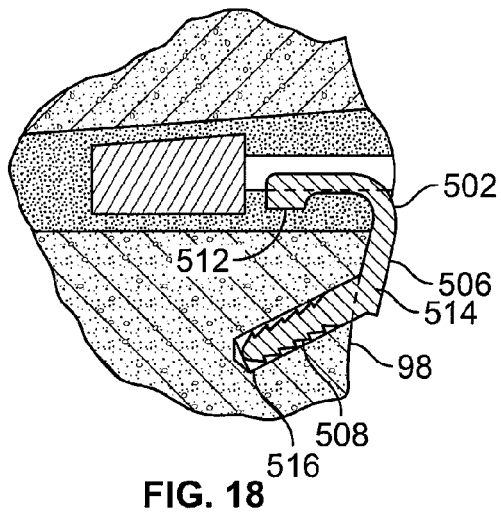
FIG. 18 is a partial cross-sectional side view of the implant retention device and spinal section of FIG. 17.
Figure 19:
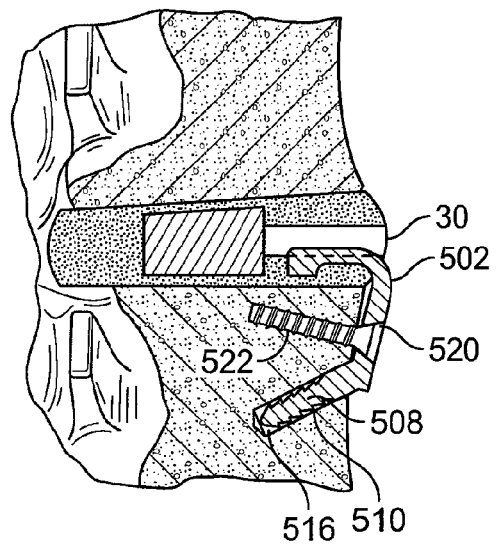
FIG. 19 is a partial cross-sectional side view of an eighth embodiment of an implant retention device showing the implant retention device mounted to a vertebra of a spinal section and inserted in an annular opening, with a nuclear implant inserted in a nuclear space of the spinal section.

As shown in FIG. 14, the integral fastener 508 projects from the mounting portion 506 and is positioned generally adjacent the center point of the V-shaped rigid member 502. Alternatively, the integral fastener 508 may project from anywhere along the length of the mounting portion 506. For example, the integral fastener 508 may be positioned at a distal end 514 of the mounting portion 506, such as shown in FIGS. 17-18. In this embodiment, the integral fastener 508 projects at a generally 45 degree angle from the terminal end 514 of the mounting portion 506, with the fastener 508 having ridges 510 configured for a press fit insertion. Again, the integral fastener 508 may project at other angles from the mounting portion 506 and a mounting hole 516 may be pre-drilled to accommodate the integral fastener 508. By another optional approach, an additional discrete fastener 522 may be used in conjunction with the described embodiments, such as shown in FIG. 19, to provide additional means for securing the implant retention device 500 to the lower vertebral body 44. A mounting aperture 520 is formed in the mounting portion 506 to accommodate the additional discrete fastener 522. The aperture 520 is preferably mounted centrally in the mounting portion 506 of the V-shaped rigid member 502, however other positions are contemplated. The fastener 522 is preferably a threaded fastener, such as a bone screw, or other fastener known in the art. The fastener 522 is inserted through the aperture 520 and into the lower vertebral body 44. The fastener 522 may be positioned at an angle to the mounting portion 506, and is positioned so as to not interfere with the integral fastener 508. The aperture 520 may be contoured or angled to facilitate an angled position of the discrete fastener 522. In addition, the integral fastener 508 may be hollowed and split to accommodate an expansion member therein, such as described and shown in FIG. 16.

Figure 20:
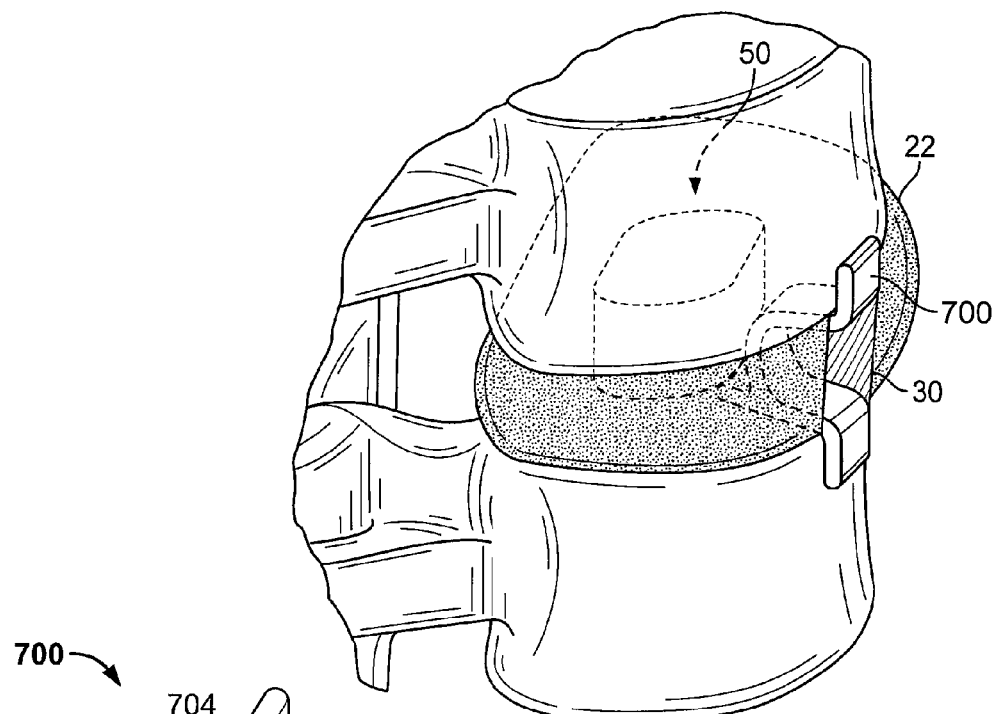
FIG. 20 is a perspective view of a ninth embodiment of an implant retention device showing the implant retention device inserted in an annular opening of a spinal section, with a nuclear implant inserted in a nuclear space of the spinal section.
Figure 21:
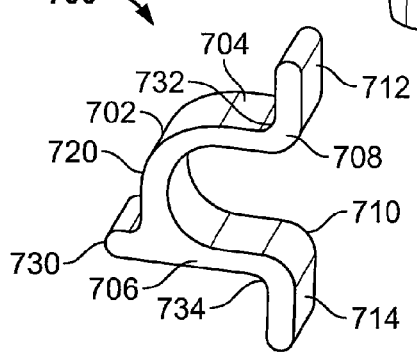
FIG. 21 is a perspective view of the implant retention device of FIG. 20.
Figure 22:
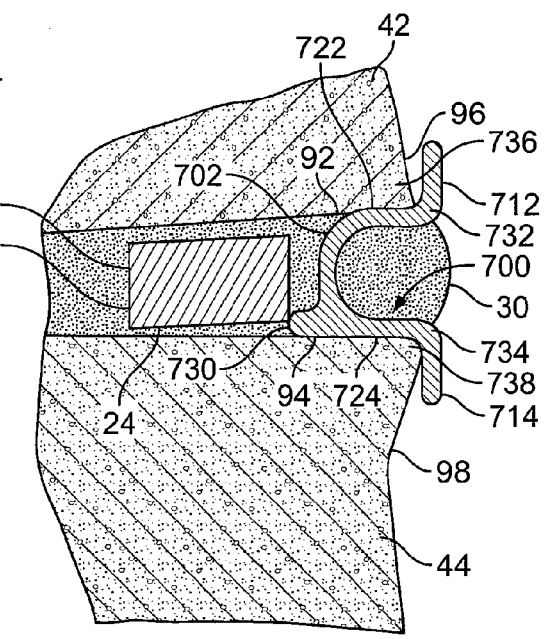
FIG. 22 is a partial cross-sectional side view of the implant retention device and spinal section of FIG. 20.

Referring now to FIGS. 20-22, an additional embodiment for an implant retention device is shown. The implant retention device 700 is comprised of a U-shaped resilient member 702 having an upper 704 and lower 706 compressible prong connected by a curved center portion 720. The implant retention device 700 may be formed, for example, from a resilient biocompatible polymer or other material, such as Nitinol. Each terminal end 708, 710 of the prongs 704, 706 of the U-shaped member 702 has an end projection 712, 714 extending therefrom. The end projections 712, 714 extend generally transverse to the prongs 704, 706 such that an upper corner portion 732 and a lower corner portion 734 are formed between each of the prongs 704, 706 and the respective end projections 712, 714. Each prong 704, 706 and the curved center portion 720 of the U-shaped resilient member 702 are configured to be compressed using, for example, an instrument, to reduce the span of the implant retention device 700 such that the U-shaped member 702 can be inserted through the annular opening 30, with the curved center portion 720 leading during insertion. The compressed U-shaped resilient member 702 is inserted through the annular opening 30 and at least partially through the annulus and into the nuclear space 24 until the end projections 712, 714 are positioned generally adjacent the exterior surface 96, 98 of the vertebral bodies 42, 44. The prongs 704, 706 are then released from the instrument and allowed to expand to their original position. After insertion and release, the exterior upper surface 722 of the upper prong 704 is positioned in mating contact with an end plate surface 92 of the upper vertebral body 42 and the exterior lower surface 724 of the lower prong 706 is in mating contact with an end plate surface 94 of the lower vertebral body 44. When the prongs 704, 706 expand, the end projections 712, 714 extending from the prongs 704, 706 engage in mating contact with the exterior surface 96, 98 of the upper 42 and lower 44 vertebral bodies. In addition, the upper corner portion 732 of the implant retention device 700 engages with and fits about a corresponding corner portion 736 of the upper vertebral body 42, and the lower corner portion 734 of the implant retention device 700 engages with and fits about a corresponding corner portion 738 of the lower vertebral body 44. The implant retention device 700 is thereby secured in position, with the end projections 712, 714 limiting the device from fully entering the nuclear space 24, such as shown in FIG. 22.

A contact member 730 projects from the lower prong 706 of the U-shaped member 702 adjacent the curved center portion 720, with the contact member 730 directed toward the bottom portion 54 of the nuclear implant 50 when the implant retention device 700 is inserted into the annular opening 30. If the nuclear implant 50 moves toward the implant retention device 700, the bottom portion 54 will contact the contact member 730 to restrict further movement of the implant 50 toward the annular opening 30. Although the implant retention device 700 is shown with the contact member 730 directed to the bottom portion 54, it should be noted that the implant retention device 700 may be inserted into the annular opening 30 with the contact member 730 directed to the top portion 52 of the implant 50. However, in an alternative embodiment with a two-part articulating implant as described above, the configuration shown in FIGS. 20-22 is preferred. Because the top shell of the implant includes a concave recess that mates with a dome surface of the bottom shell, the top shell experiences more rotation and translation as it articulates relative to the bottom shell, with the bottom shell remaining in a more stationary position. With the contact member 730 contacting only the bottom shell, the contact member 730 does not interfere with the articulation of the top shell relative to the bottom shell, which also results in less wear on the implant. In addition, the forces created by any contact between the implant 50 and the implant retention device 700 will not cause the upper 704 and lower 706 prongs to recompress such that the device 700 will be expelled from the annular opening 30. To remove the implant retention device 700, an instrument can compress the prongs 704, 706 to reduce the span of the device 700 so that it may withdrawn through the annular opening 30.

Figure 23:
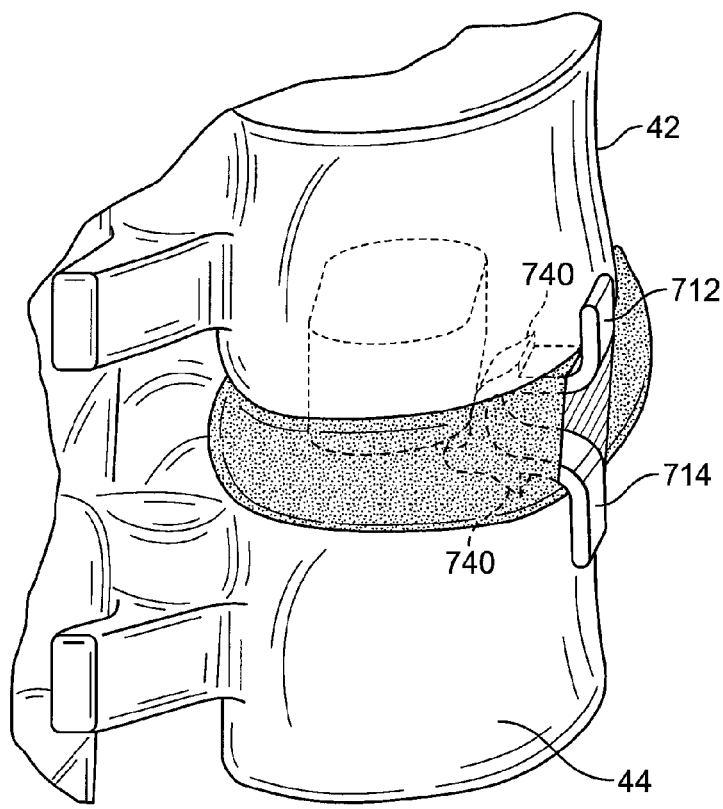
FIG. 23 is a perspective view of a tenth embodiment of an implant retention device showing the implant retention device inserted in an annular opening of a spinal section, with a nuclear implant inserted in a nuclear space of the spinal section.
Figure 24:
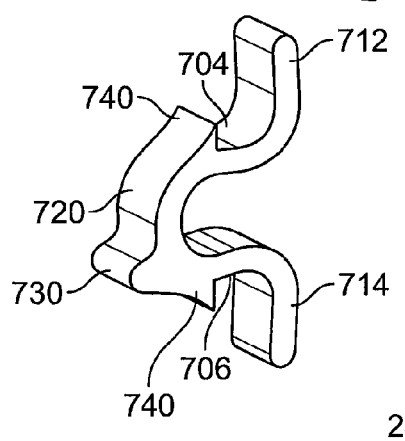
FIG. 24 is a perspective view of the implant retention device of FIG. 23.
Figure 25:
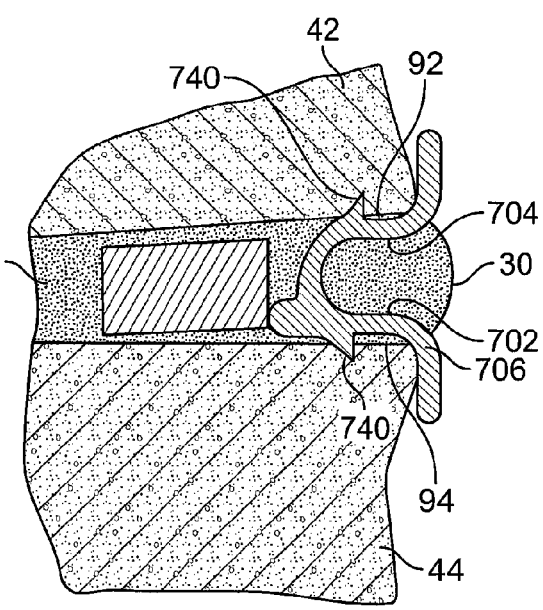
FIG. 25 is a partial cross-sectional side view of the implant retention device and spinal section of FIG. 23.

By another optional approach, the U-shaped member 702 may further include at least one barb 740 projecting therefrom, as shown in FIGS. 23-25. At least one barb 740 may project from each of the upper 704 and lower 706 prongs. The barb 740 is preferably generally triangle-shaped with a sharp point projecting away from the prong, such that the barb 740 penetrates the end plate 92, 94 of the vertebral body 42, 44 from within the nuclear space 24, as shown in FIG. 25. The barb 740 thus secures the implant retention device 700 to the vertebral bodies 42, 44 to restrict any movement or dislodging of the implant retention device 700.

Figure 26:
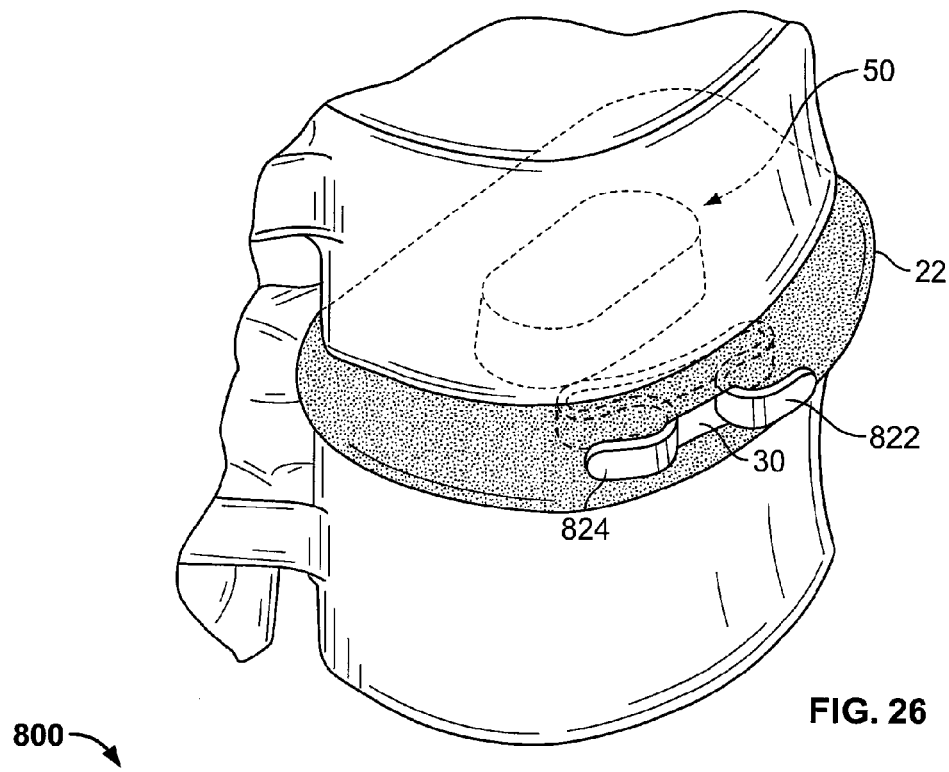
FIG. 26 is a perspective view of an eleventh embodiment of an implant retention device showing the implant retention device inserted in an annular opening of a spinal section, with a nuclear implant inserted in a nuclear space of the spinal section.
Figure 27:
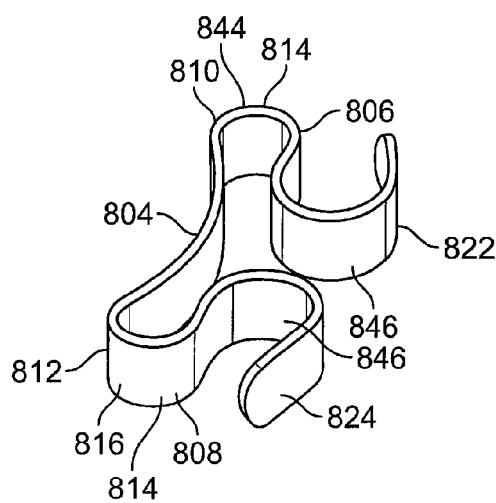
FIG. 27 is a perspective view of the implant retention device of FIG. 26.
Figure 28:
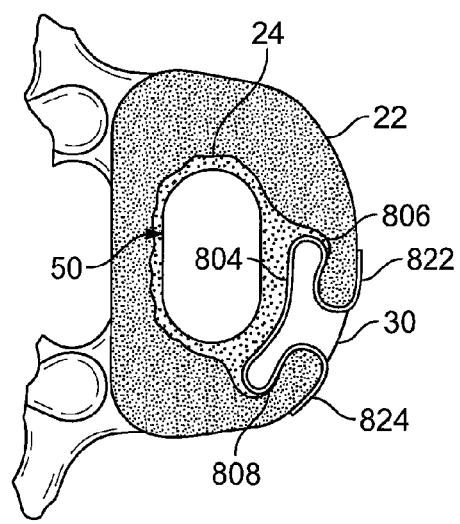
FIG. 28 is a cross-sectional top view of the spinal section of FIG. 26 showing the implant retention device and the nuclear implant.

Another embodiment of the implant retention device 800 is shown in FIGS. 26-28. In this embodiment, the implant retention device 800 includes an elongated blocking member 804, with a pair of S-shaped hooking members 806, 808 projecting from ends 810, 812 of the elongated blocking member 804. The elongated blocking member has a slight concavity as it extends between the ends 810, 812, which more closely mimics the interior shape of the annular wall 22. The implant retention device 800 is symmetrical about a center line of the elongated blocking member 804. The S-shaped hooking members 806, 808 include a first curved portion 844 connected to ends 810, 812 of the elongated blocking member 804 and a second curved portion 846 extending from the first curved portion 844 and ending in terminal ends 822, 824. The implant retention device 800 may be formed, for example, from a resilient biocompatible polymer or other material, such as Nitinol.

To insert the implant retention device 800 into the annular opening 30, the ends 810, 812 of the elongated blocking member 804 are pulled inwardly toward each other using, for example, an instrument, such that the elongated blocking member 804 folds generally along its center line. Terminal ends 822, 824 of each S-shaped hooking member may also optionally be pulled toward each other to further facilitate insertion through the annular opening 30. The elongated blocking member 804 is thus compressed such that the span of the implant retention device 800 is less than the width of the annular opening 30. The annular opening 30 is sized to have a height and width greater than the height and width of the compressed implant retention device 800 such that the compressed implant retention device 800 can fit through the annular opening 30. The compressed elongated blocking member 804 and lower ends 814, 816 of each S-shaped hooking member 806, 808 are then inserted through the annular opening 30 and at least partially into the nuclear space 24, with the terminal ends 822, 824 of the second curved portion 846 of each S-shaped hooking member 806, 808 remaining on the outside of the annulus 22. Once the terminal ends 822, 824 of each S-shaped hooking member 806, 808 are generally adjacent the exterior of annulus 22, the implant retention device 800 is then released from the compressed position and is allowed to expand to its original position. Once expanded, the elongated blocking member 804 covers the annular opening 30 from the interior of the nuclear space 24 and has a span greater than the annular opening 30 to obstruct the exit path of the nuclear implant 50. If the implant 50 moves toward the annular opening 30, the implant retention device 800 will prevent the implant 50 from exiting through the annular opening 30. In addition, any contact between the implant 30 and the device 800 within the nuclear space will not cause the device 800 to recompress and expel from the annular opening. The terminal ends 822, 824 of each S-shaped hooking member 806, 808 remain on the exterior of the annulus 22 and function to project from the annular opening 30 and hook onto the exterior surface of the annulus 22. The terminal ends 822, 824 of each S-shaped hooking member 806, 808 hook onto the annulus 22 to limit movement of the implant retention device 800 and maintain the device 800 in position.

Figure 29:
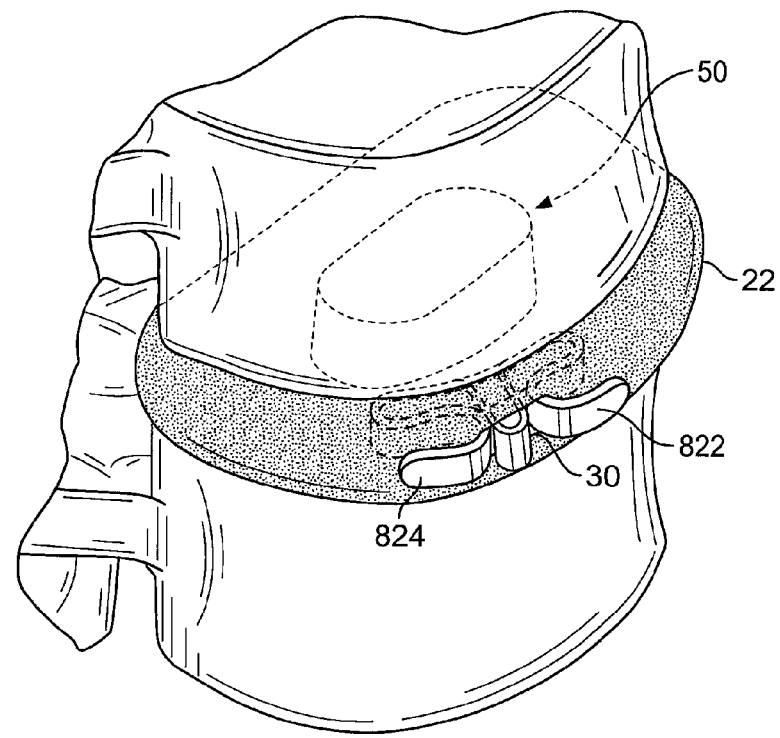
FIG. 29 is a perspective view of a twelfth embodiment of an implant retention device showing the implant retention device inserted in an annular opening of a spinal section, with a nuclear implant inserted in a nuclear space of the spinal section.
Figure 30:
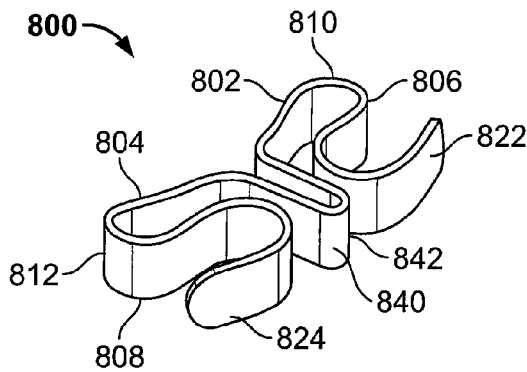
FIG. 30 is a perspective view of the implant retention device of FIG. 29.
Figure 31:
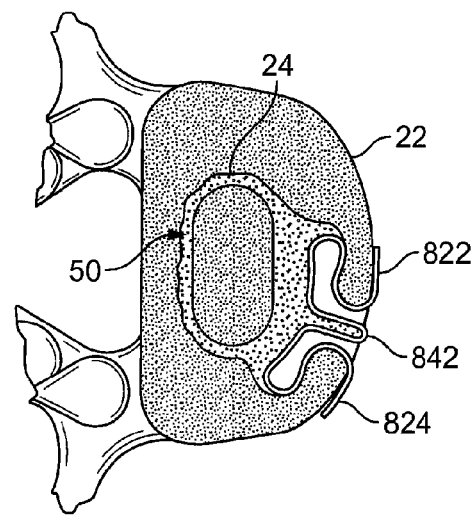
FIG. 31 is a cross-sectional top view of the spinal section of FIG. 29 showing the implant retention device and the nuclear implant.

By another optional approach, and referring to FIGS. 29-31, the elongated blocking member 804 may include an additional center bend 840 therein, with the bend 840 preferably extending generally from the elongated blocking member 804 to the terminal ends 822, 824 of the S-shaped hooking members 806, 808. To insert the implant retention device 800, the ends 810, 812 of the elongated blocking member 804 are again pulled inwardly toward each other using, for example, a tool or instrument, such that the elongated blocking member 804 folds generally about the center bend 840. The device 800 is then held in the compressed position using, for example, the instrument. The compressed elongated blocking member 804, including the lower end of the center bend 840, and lower ends 814, 816 of each S-shaped hooking member 806, 808 are then inserted through the annular opening 30 and at least partially into the nuclear space 24, with the terminal ends 822, 824 of each S-shaped hooking member 806, 808 remaining on the outside of the annulus 22. Once inserted, the device 800 is released from the compressed position and allowed to expand to its original configuration, with the terminal ends 822, 284 of the S-shaped hooking members 806, 808 hooking onto the annulus. Once expanded, the elongated blocking member 804 covers the annular opening 30 from inside the nuclear space 24 and has a span greater than the annular opening 30 to obstruct the exit path of the nuclear implant 50. An end portion 842 of the center bend 840 projects from the annular opening 30. Again, if the implant 50 moves toward the annular opening 30, the implant retention device 800 will prevent the implant 50 from exiting through the annular opening 30. In addition, any contact between the implant 30 and the device 800 within the nuclear space 24 will not cause the device 800 to recompress and expel from the annular opening. The terminal ends 822, 824 of each S-shaped hooking member 806, 808 remain on the exterior of the annulus 22 and function to project from the annular opening 30 and hook onto the annulus 22. The terminal ends 822, 824 of each S-shaped hooking member 806, 808 hook onto the annulus 22 to retain the implant retention device 800 in position.

The center bend 840 facilitates removal of the implant retention device 800. The end portion 842 of the center bend 840 that projects from the annular opening 30 can be grasped with a tool and pulled outwardly, causing ends 810, 812 of the elongated blocking member 804 to move inwardly toward each other such that the implant retention device 800 compresses to reduce its width to fit through the annular opening 30.

Figure 32:
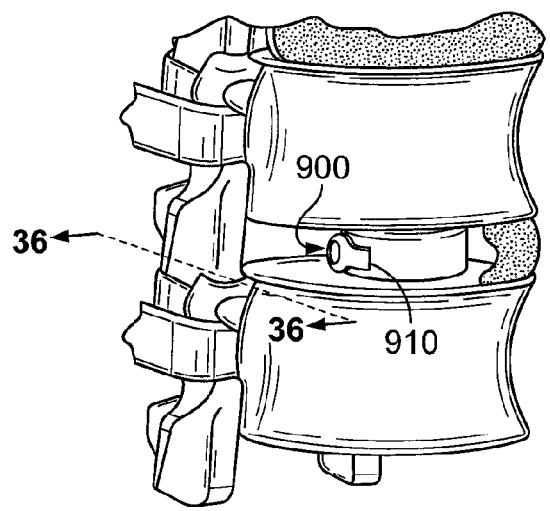
FIG. 32 is a perspective view of a thirteenth embodiment of an implant retention device showing the implant retention device inserted into a nuclear space of a spinal section with a nuclear implant therein.
Figure 33:
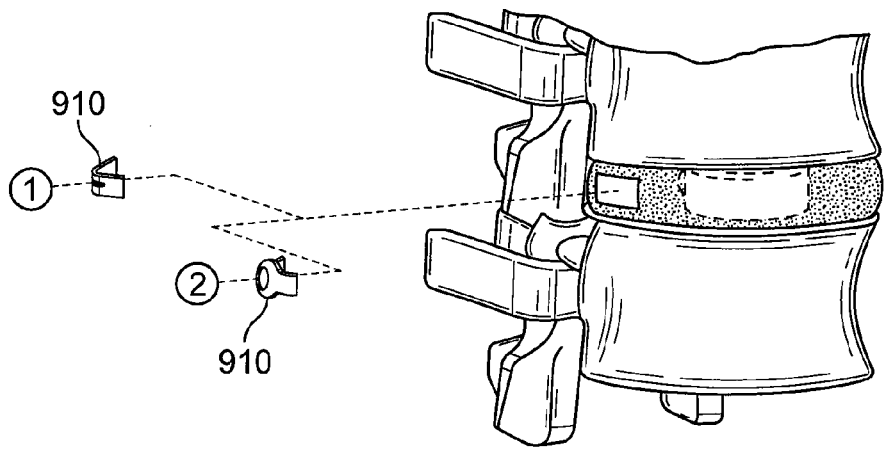
FIG. 33 is an exploded perspective view of the implant retention device and spinal section of FIG. 32 showing the device in a first expanded position and a second compressed position prior to insertion into the nuclear space.
Figure 34:
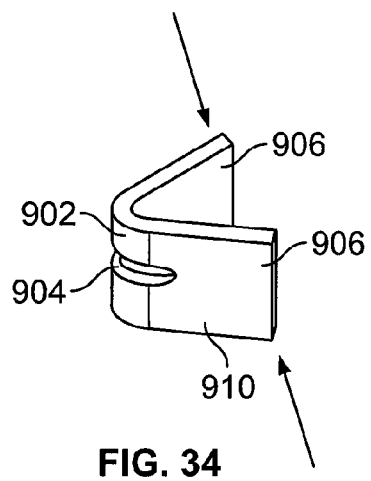
FIG. 34 is a perspective view of the implant retention device of FIG. 33 in the compressed position.
Figure 35:
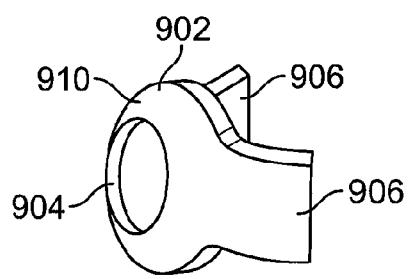
FIG. 35 is a perspective view of the implant retention device of FIG. 33 in the expanded position.
Figure 36:
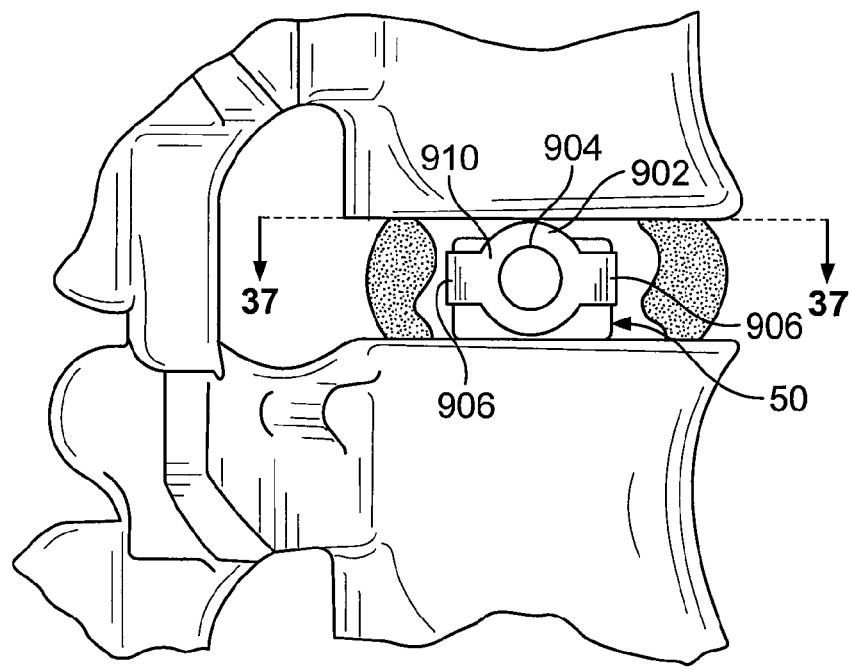
FIG. 36 is a partial side view of the implant retention device and spinal section of FIG. 32 taken along line 36-36 thereof.

By another approach, the implant retention device may be located within the nuclear space. Referring now to FIGS. 32-37, an embodiment of the implant retention device 900 is shown. The implant retention device 900 is comprised of a compressible shield 910. The shield is formed, for example, from a resilient biocompatible polymer or other material, such as Nitinol. The compressible shield 910 has a center ring portion 902 with a hole 904 therethrough, and wing portions 906 extending laterally from opposing sides of the ring portion 902. The center ring portion 902 has a diameter generally greater than the height of the wing portions 906. As shown in FIGS. 33 and 35, the compressible shield 910 has a first expanded position. The compressible shield 910 is then compressed into a compressed position using, for example, an instrument, to fold the wing portions 906 inwardly toward each other to reduce the lateral span of the compressible shield 910. The folding in of the wing portions 906 also reduces the diameter of the center ring portion 902, as shown in FIGS. 33 and 34.

Figure 37:
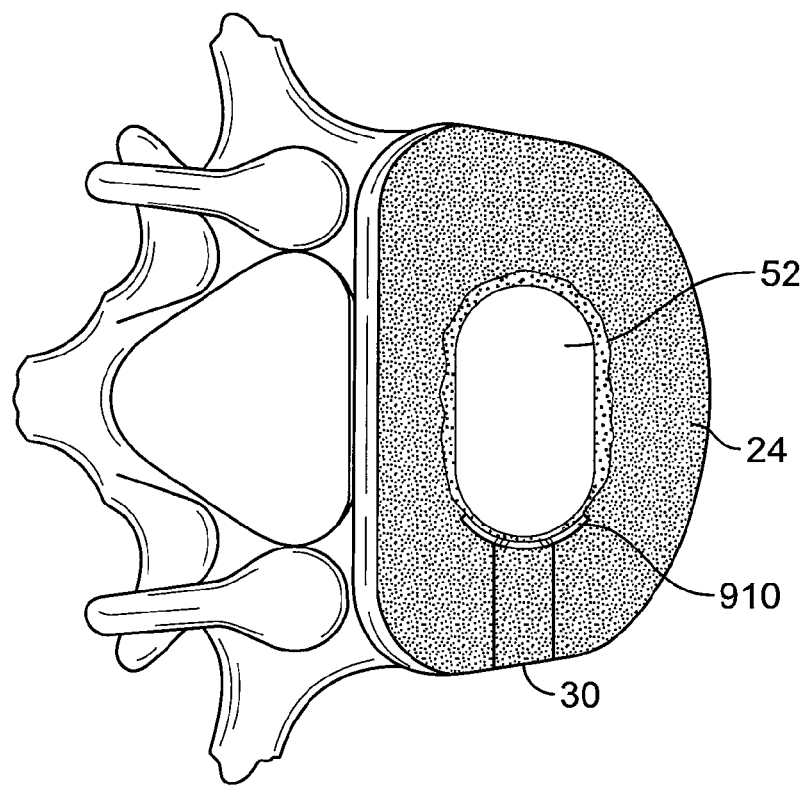
FIG. 37 is a cross-sectional top view of the spinal section of FIG. 36 taken along line 37-37 thereof and showing the nuclear implant and the implant retention device.

As a result, the shield profile is reduced such that the size of the compressible shield 910 is less than the size of the annular opening 30 so that the shield 910 can be inserted through the annular opening 30. The compressed shield 910 is then inserted through the annular opening 30 using the instrument and deposited into the nuclear space 24. The shield 910 is positioned adjacent the nuclear implant 50 and between the implant 50 and the annular opening 30. The shield 910 is then released from the instrument and allowed to expand. In the expanded position, the ring portion 902 expands to a height greater than the height of the annular opening 30. The wing portions 906 also expand such that the compressible shield 910 preferably has a width greater than the width of the annular opening 30. The force of the implant 50 against the shield is generally incapable of recompressing the shield. As a result, the shield will obstruct the annular opening 30 to prevent the nuclear implant 50 from being expelled from the nuclear space 24, such as shown in FIGS. 32 and 37.

Figure 38:
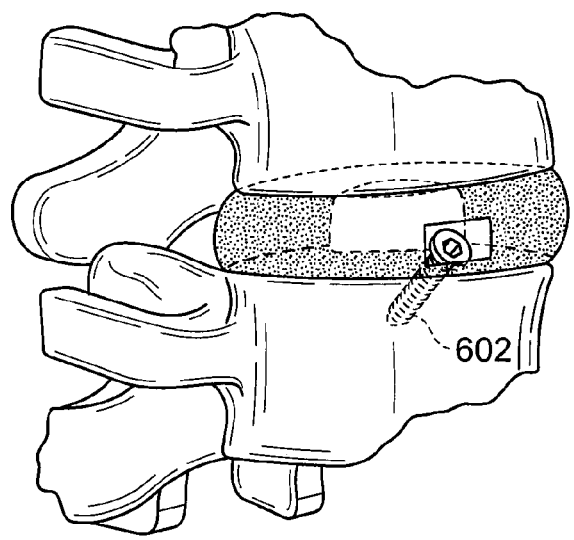
FIG. 38 is a perspective view of a fourteenth embodiment of an implant retention device mounted to a vertebra of a spinal section, with a nuclear implant inserted in a nuclear space of the spinal section.
Figure 39:
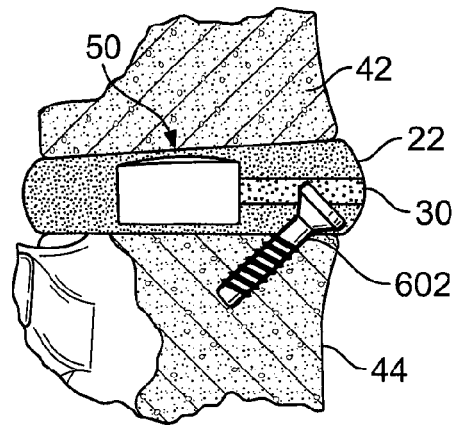
FIG. 39 is a partial cross-sectional side view of the spinal section of FIG. 38 showing the implant retention device and nuclear implant.
Figure 40:
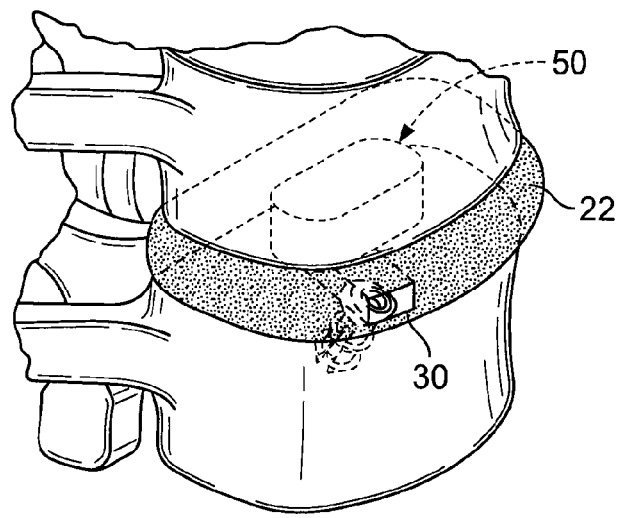
FIG. 40 is a perspective view of a fifteenth embodiment of an implant retention device mounted to a vertebra of a spinal section, with a nuclear implant inserted in a nuclear space of the spinal section.

By another approach, a single fastener 602 may be used to restrict movement of the implant 50, such as shown in FIGS. 38-39. The fastener 602 is driven into to the lower vertebral body 44, with the fastener 602 positioned to interfere with the annular opening 30. The fastener 602 may also penetrate a portion of the annulus 22. A portion of the fastener 602 partially blocks the annular opening 30 to interfere with any movement of the implant 50 toward the annular opening 30. Alternatively, the fastener 602 may be driven through the upper vertebral body 42. The portion of the fastener 602 obstructing the annular opening is preferably aligned with only one portion 52, 54 of the implant 50 such that when a two-piece articulating implant is used, the fastener allows for relative movement between the articulating pieces. The fastener 602 may be a threaded screw or may comprise a member having concentric ridges thereon for being press fit into a pre-drilled mounting hole.

Figure 44:
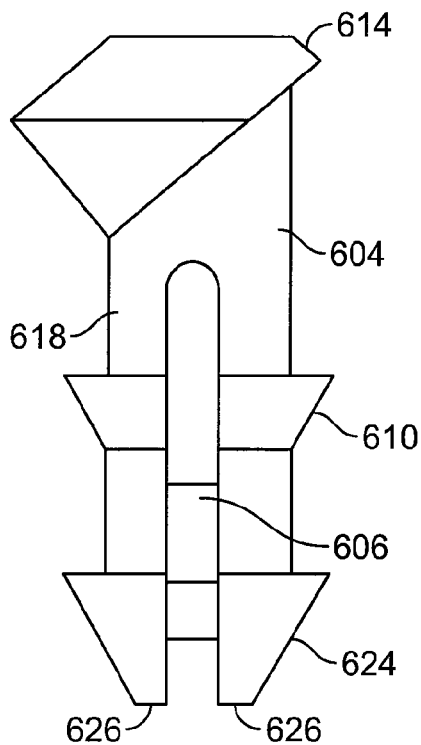
FIG. 44 is a side view of the implant retention device of FIG. 42.
Figure 45:
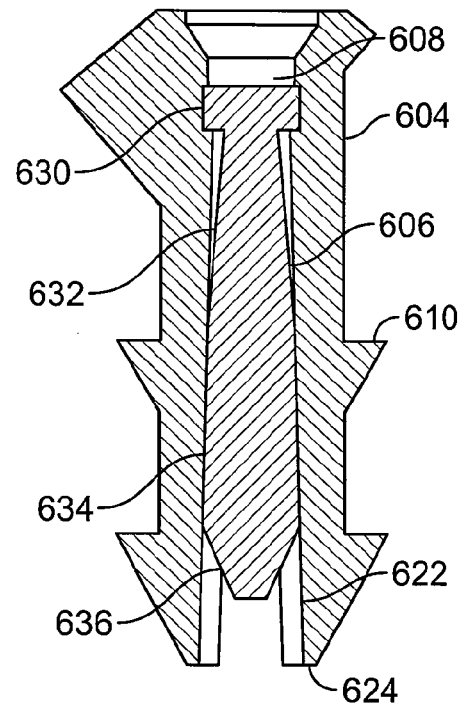
FIG. 45 is a cross-sectional side view of the implant retention device of FIG. 44.

Alternatively, a two-piece fastener 612 may be used, with the fastener 612 comprised of a split and hollowed outer shell 604 and an expansion member 606 that is inserted in a longitudinal hole 608 of the outer shell 604. Referring now to FIGS. 40-45, the outer shell 604 includes a head portion 614 with an opening 616 therethrough for receiving the expansion member 606. A shaft portion 618 of the outer shell 604 includes a plurality of concentric ridges 610 to allow for a press fit insertion into a pre-drilled mounting hole 620 in the lower vertebral body 44. The shaft portion 618 is split such that a pair of longitudinal cut-outs 622 extend from a tip 624 of the outer shell 604 up along a portion of the length of the shaft portion 618, thus separating the shaft portion 618 into a pair of curvilinear length portions 626. To insert the shaft portion 618 in the mounting hole 620, the curvilinear length portions 626 are compressed together at the tip 624 to reduce the diameter of the tip 624 to clear the mounting hole 620 sidewalls. The shaft portion 618 is then press fit into the mounting hole 620, with the head portion 614 positioned to interfere with the annular opening 30 and exit path of the implant 50. The head portion 614 is asymmetrical, with a semi-circular edge that is generally positioned to project into the exit path of the annular opening 30 and an elongated curved edge 640 that is positioned generally adjacent the lower vertebral body 44. In addition, as shown in FIG. 44, the head portion 614 and the shaft portion 618 mate in an angled configuration. As a result, the head portion 614 is angled to create a minimal profile while still providing a vertical face to prevent dislodgment of the implant 50.

Once the outer shell 604 is positioned, the expansion member 606 is then driven through the opening 616 in the head portion 614. The expansion member 606 includes a head portion 630 and a shaft portion 632, with the shaft portion 632 widening towards a base portion 634 and then narrowing towards the tip 636. As the expansion member 606 is driven through the opening 616 in the head portion 614 and into the hole 608 of the shaft portion 618 of the outer shell 604, the wide base portion 634 causes the curvilinear length portions 626 of the shaft portion 618 to splay outwardly. As a result, the concentric ridges 610 engage with the walls of the mounting hole 620 to secure the fastener 612 in place. The fastener 612 is then positioned to at least partially block the annular opening 30 to interfere with any movement of the implant 50 toward the annular opening 30.

Figure 46:
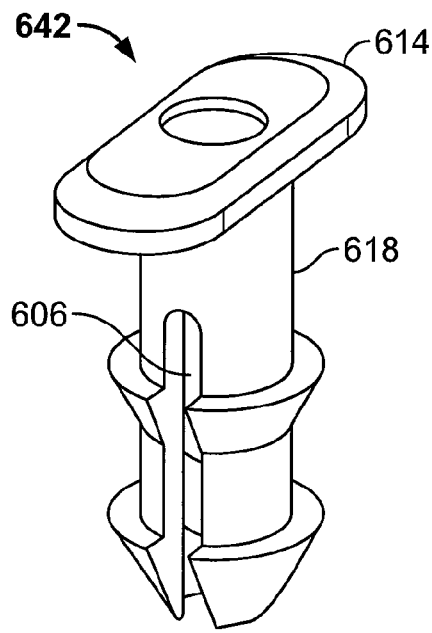
FIG. 46 is a perspective view of a sixteenth embodiment of an implant retention device.
Figure 47:
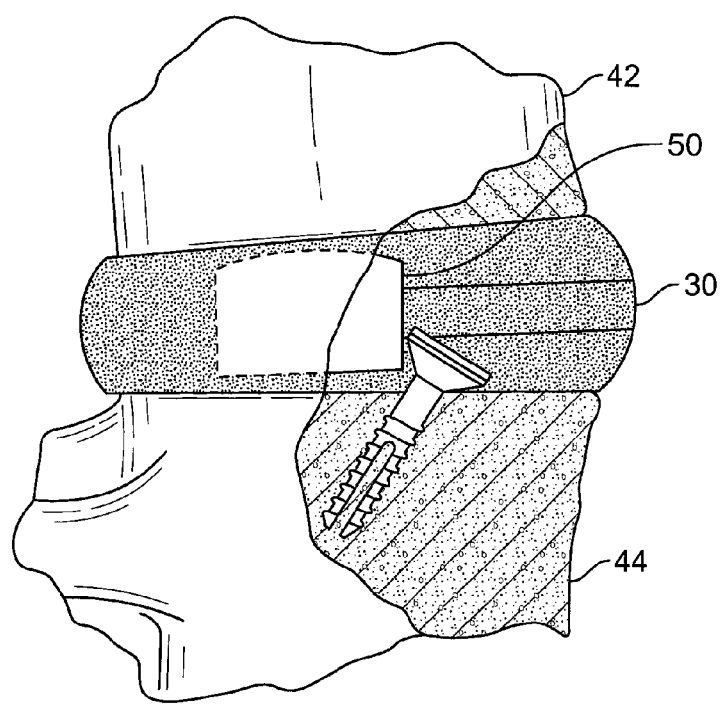
FIG. 47 is a partial cross-sectional view of a seventeenth embodiment of an implant retention device mounted to a vertebra of a spinal section, with a nuclear implant inserted in a nuclear space of the spinal section.
Figure 48:
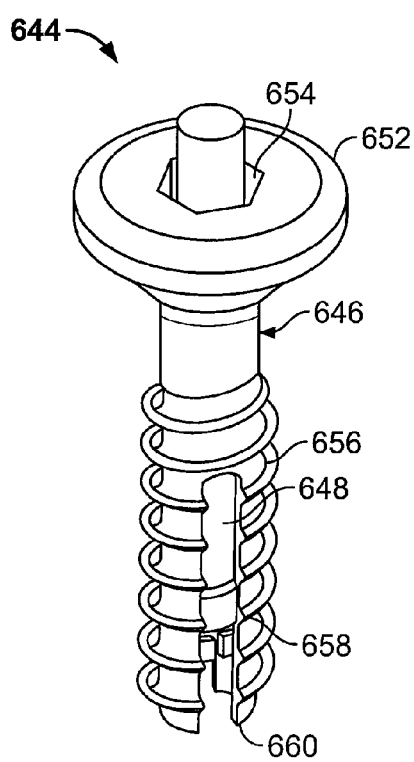
FIG. 48 is a perspective view of the implant retention device of FIG. 47.
Figure 49:
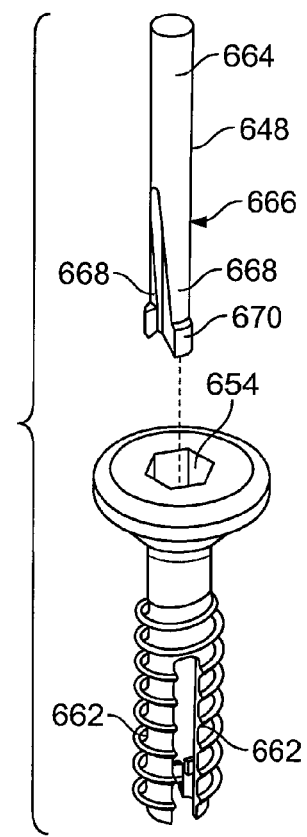
FIG. 49 is an exploded perspective view of the implant retention device of FIG. 48.
Figure 50:
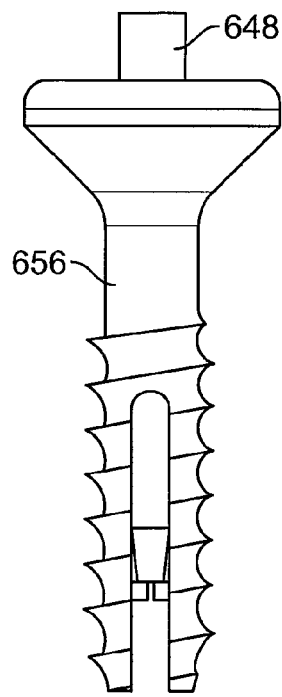
FIG. 50 is a side view of the implant retention device of FIG. 49.
Figure 51:
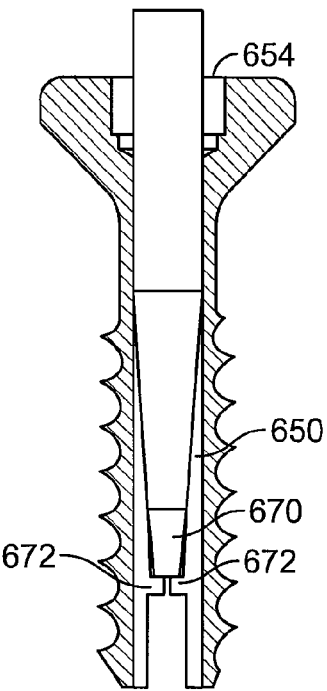
FIG. 51 is a first cross-sectional side view of the implant retention device of FIG. 50.
Figure 52:
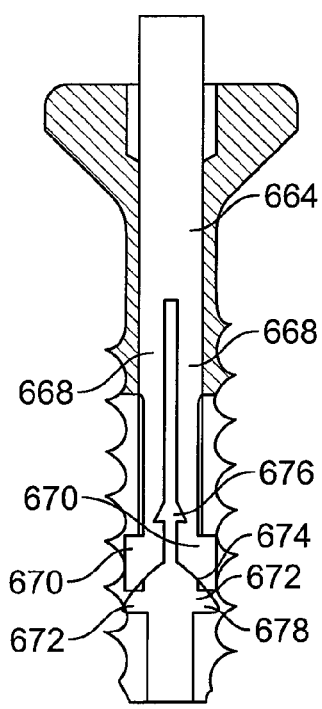
FIG. 52 is a second cross-sectional side view of the implant retention device of FIG. 50.

Referring now to FIG. 46, an alternate embodiment of a fastener 642 is shown. The shaft portion 618 and expansion member 606 have generally the same configuration as the fastener of FIG. 42, however the head portion 614 has a different configuration. In this embodiment, the head portion 614 has an elongated oval or racetrack shape to provide for an increased surface area for at least partially obstructing the exit path of the annular opening 30 to interfere with any movement of the implant 50 toward the annular opening 30.

By another optional approach, and referring now to FIGS. 47-52, a threaded two-piece fastener 644 is shown. As with the fastener 612 described above, the fastener 644 is comprised of a split and hollowed outer shell 646 and an expansion member 648 that is inserted in a longitudinal hole 650 of the outer shell 646. The outer shell 646 includes a generally circular head portion 652 with an opening 654 therethrough for receiving the expansion member 648. A shaft portion 656 of the outer shell 646 is threaded to be driven into the lower vertebral body 44. The shaft portion 656 is split such that a pair of longitudinal cut-outs 658 extend from a tip 660 of the outer shell 646 up along a portion of the length of the shaft portion 656, thus separating the shaft portion 656 into a pair of curvilinear length portions 662. To insert the outer shell 646 into the vertebral body 644, the shaft portion 656 is driven into the vertebral body 644, with the threaded shaft portion 656 following a helical path as it is screwed into the vertebral body 644. The head portion 652 of the outer shell 646 is preferably positioned to interfere with the exit path of the implant 50.

Once the outer shell 646 is positioned, the expansion member 648 is then inserted through the opening 654 in the head portion 652 and pushed into the longitudinal hole 650. The expansion member 648 comprises a main shaft portion 664 and a pronged end portion 666 comprised of a pair of forks 668 with barbs 670 on distal ends thereof. The barbs 670 are generally aligned with the cut-outs 658 of the shaft portion 656. The shaft portion 656 of the outer shell 646 includes a pair of angled projections 672 extending from each of the curvilinear length portions 662. As the barbs 670 approach the projections 672, the barbs 670 slide down the angled surface 674 of the projections 672 and are splayed outwardly. As the expansion member 648 is further inserted into the longitudinal hole 650, the barbs 670 continue move along the angled surface 674 and splay outwardly until a notch 676 along the length of the forks 668 engages with an end 678 of the angled projection 672. The barbs 670 are then fully deployed to further limit rotation or movement of the fastener 644. Once inserted, the fastener 644 is positioned to at least partially block the annular opening 30 to interfere with any movement of the implant 50 toward the annular opening 30.

Figure 53:
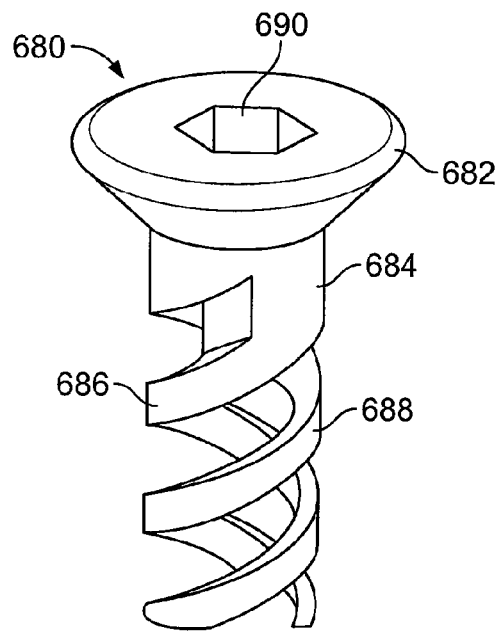
FIG. 53 is a perspective view of an eighteenth embodiment of an implant retention device.
Figure 54:
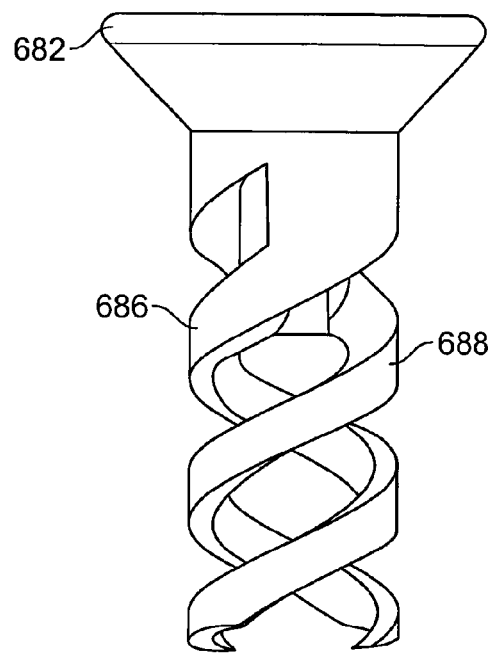
FIG. 54 is a side view of the implant retention device of FIG. 53.
Figure 55:
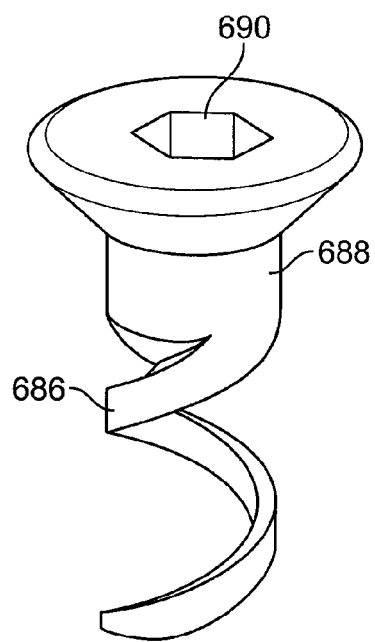
FIG. 55 is a perspective view of a nineteenth embodiment of an implant retention device.
Figure 56:
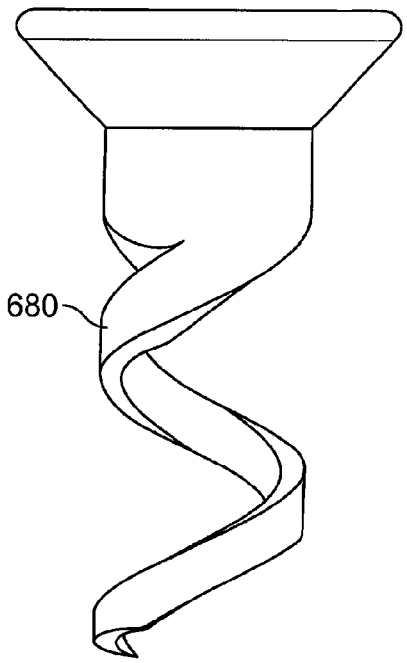
FIG. 56 is a side view of the implant retention device of FIG. 55.

Referring now to FIGS. 53-54, an alternate fastener 680 is shown. The fastener 680 comprises a generally circular head portion 682 and a shaft portion 684 comprised of a pair of helical prongs 686, 688 arranged in a double helix configuration and extending from the head portion 682. The pair of helical shaft members define the outer circumference of the shaft portion, with the interior being generally hollow which results in less destruction of the end plate of the vertebral body. The shaft portion 684 of the fastener 680 is driven into the vertebral body 44 by inserting an instrument in a hole 690 in the head portion 682 to rotate the fastener 680 and drive it into the vertebral body (not shown). The fastener 680 is preferably positioned to interfere with the exit path of the implant 50. Alternatively, and referring now to FIGS. 55-56, a single helical prong 686 may be used.

Figure 57:
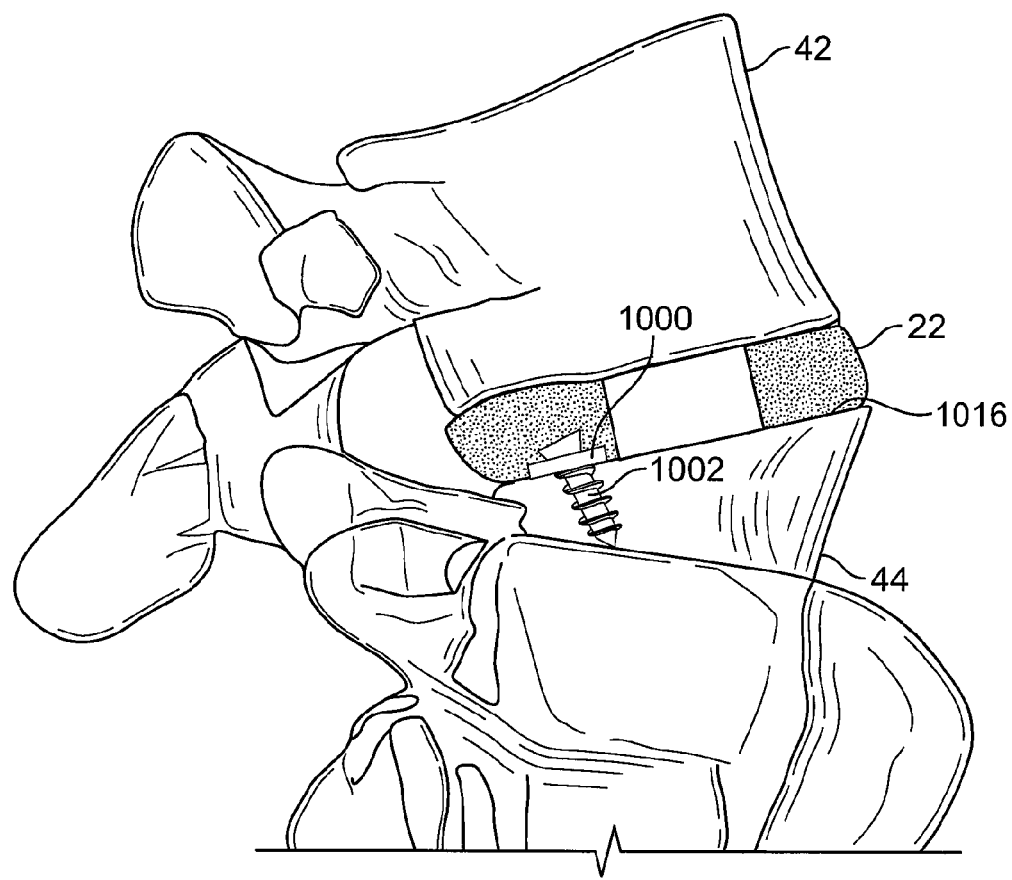
FIG. 57 is a perspective view of a twentieth embodiment of an implant retention device mounted to a vertebra of a spinal section with a nuclear implant inserted in a nuclear space of the spinal section.

Referring now to FIG. 57, the implant retention device may comprise a separate bumper member for obstructing the annular opening 30. The bumper member may take the form of an annular washer 1000, which is fastened to a superior surface 1016 of a vertebra 44 with a fastener, such as a screw 1002. The bumper member is shaped and sized to confront at least a portion of the implant 50. That way, when a two-piece implant is used, the bumper member is positioned to contact just one of the pieces of the implant and the implant is not impeded from articulating by the bumper. The bumper member may take a variety of forms effective to obstruct the annular opening 30, as would be apparent to those skilled in the art.

Figure 58:
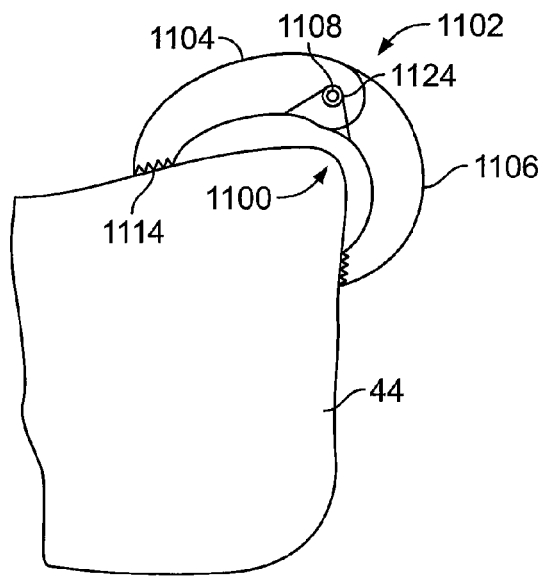
FIG. 58 is a partial side view of a twenty-first embodiment of an implant retention device mounted to a vertebra.
Figure 59:
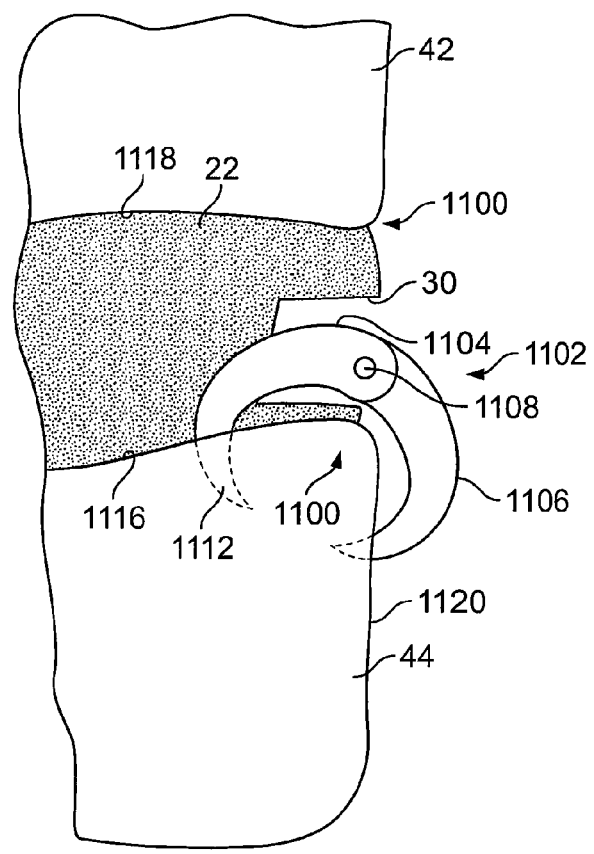
FIG. 59 is a partial side view of a twenty-second embodiment of an implant retention device mounted to a vertebra.

In two related embodiments shown in FIGS. 58 and 59, the implant retention device may take the form of a blocking member that may be manipulated to or shaped to conform to the contour of a vertebra. The blocking member may be formed from a single shapeable body, such as a malleable metal strip that may be bent to conform to the contour of a vertebral edge 1100. Alternatively, the blocking member may be formed from two or more members that are movably connected to one another. In a preferred embodiment, the blocking member is a clip 1102 formed from a pair of arcuate bodies 1104, 1106 connected by a pivot connection 1108. Each arcuate body 1104, 1106 has a fastening portion for engaging the vertebra 44. The fastening portion may take the form of a spike-shaped protrusion 1112, as shown in FIG. 59, or an engagement surface with a plurality of protrusions, such as teeth 1114 shown in FIG. 58. One fastening portion engages an interior portion of the vertebra, such as the superior or inferior face of the vertebra 1116, 1118, while the other fastening portion engages an outer face of the vertebra 1120. With this configuration, the clip 1102 is disposed on the outer edge of a vertebra 1100, with a portion of the clip 1102 protruding at least partially into the annular window 30, and another portion of the clip 1102 engaged with an outer face of the vertebra 1120. The portion of the blocking member protruding into the annular window 30 includes a blocking portion which obstructs the annular opening to interfere with movement of the implant 50 through the annular opening 30. Because the clip bodies 1104, 1106 are connected via a pivot connection 1108, the bodies 1104, 1106 are adjustable with respect to one another, and thus may be conformed to follow the contour of the superior or inferior vertebral edge 1100. In addition, the clip 1102 may be provided with a bumper member for providing a blocking portion, such as a sleeve or a washer described above, which would be disposed on the portion of the clip 1102 within or adjacent the annular window 30.

The clip's pivot connection 1108 may be provided with a biasing member, such as a spring 1124 to bias the bodies 1104, 1106 and the respective fastening portions towards one another, such that the fastening portions are brought adjacent to one another to conceal or cover any sharp edges of the fastening portions. This feature helps to prevent trauma to vital tissues in the vertebral area should the clip 1102 become dislodged from the vertebra 44. In addition, the biasing member may help keep the fastening portions in contact with the vertebral bone by urging the fastening portions toward one another and thereby gripping the bone between the fastening portions.

The implant retention devices and features as described herein may be adapted for use with a variety of artificial joint arrangements other than nuclear implants. In addition, the implant retention devices and features as described herein may be adapted for use with a variety of surgical approaches. Most of the surgical approaches shown in the illustrations are from an anterior or lateral approach but are easily adaptable for a posterior approach, for example. In a posterior approach, an incision portal is made in the posterior annulus.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method for restraining a nuclear implant in an intervertebral nuclear space between adjacent upper and lower vertebrae, the method comprising:

creating a through opening in an annular wall into the nuclear space with the through opening having a height less than that of the annular wall extending between the upper and lower vertebrae such that a portion of the annular wall is left intact adjacent one of the upper and lower vertebrae above or below the opening, respectively, and the through opening extends from an outer surface to an inner surface thereof for the full thickness of the annular wall with the wall inner surface extending about the nuclear space to allow insertion of the nuclear implant into the nuclear space;

inserting the nuclear implant through the through opening in the annular wall into the nuclear space so that the nuclear implant traverses the entire thickness of the annular wall for inserting the implant into the nuclear space;

driving an elongate anchoring portion of a single, one-piece fastener into one of the adjacent vertebrae to position a radially enlarged head portion of the single, one-piece fastener in the through opening between the outer and inner surfaces of the annular wall such that the radially enlarged head portion and the intact annular wall portion adjacent the one vertebra cooperate to obstruct an exit path of the implant out from the nuclear space and through the through opening, wherein the nuclear implant is a two-piece articulating implant having upper and lower shell members and the head portion of the single fastener is positioned adjacent to at least one of the upper and lower shells.

2. The method of claim 1, wherein fastening the single, one-piece fastener to the one of the adjacent vertebrae comprises rotating the fastener and advancing the elongate anchoring portion into the one of the adjacent vertebrae.

3. The method of claim 1, further comprising predrilling a recess in the one of the adjacent vertebrae for receiving at least a portion of the elongate anchoring portion.

4. The method of claim 3, wherein the recess is predrilled in the one of the adjacent vertebrae at an inner facing surface thereof.

5. The method of claim 3, wherein fastening the anchoring portion of the fastener comprises press-fitting the elongate anchoring portion into the recess in the one of the adjacent vertebrae.

6. The method of claim 1, wherein fastening the anchoring portion of the single fastener includes inserting an expansion member into a bore in the fastener to expand the anchoring portion into fixed engagement with the one of the adjacent vertebrae.

7. The method of claim 1, wherein the single fastener is fastened to the lower one of the adjacent vertebrae.

8. The method of claim 1, wherein the head portion of the single fastener is positioned adjacent a lower portion of the nuclear implant.

9. The method of claim 1, wherein the position of the head portion of the single fastener is controlled by the depth with which the elongate anchoring portion is driven into the one of the adjacent vertebrae.

10. The method of claim 1, wherein positioning a head portion of the single fastener includes positioning a tapered inner face of the head portion between the outer and inner surfaces of the annular wall to obstruct an exit path of the implant.

11. The method of claim 1, wherein creating the through opening further comprises leaving upper and lower intact portions of the annular wall adjacent the upper and lower vertebrae above and below the opening, respectively, such that the upper and lower intact portions cooperate with the single fastener head portion to obstruct an exit path of the implant out from the nuclear space through the through opening.

12. The method of claim 1, wherein the head portion of the single fastener is positioned adjacent to the lower shell member of the nuclear implant such that only the lower shell may engage with the head portion, leaving the upper shell free to articulate with respect to the lower shell.

13. A method for restraining a nuclear implant in an intervertebral nuclear space between adjacent upper and lower vertebrae, the method comprising:

creating a through opening in an annular wall into the nuclear space with the through opening having a height less than that of the annular wall extending between the upper and lower vertebrae such that a portion of the annular wall is left intact adjacent one of the upper and lower vertebrae above or below the opening, respectively, and the through opening extends from an outer surface to an inner surface thereof for the full thickness of the annular wall with the wall inner surface extending about the nuclear space to allow insertion of the nuclear implant into the nuclear space;

inserting the nuclear implant through the through opening in the annular wall into the nuclear space so that the nuclear implant traverses the entire thickness of the annular wall for inserting the implant into the nuclear space;

driving an elongate anchoring portion of a single, one-piece fastener into one of the adjacent vertebrae to position a radially enlarged head portion of the single, one-piece fastener in the through opening between the outer and inner surfaces of the annular wall such that the radially enlarged head portion and the intact annular wall portion adjacent the one vertebra cooperate to obstruct an exit path of the implant out from the nuclear space and through the through opening, wherein the radially enlarged head portion of the single, one-piece fastener has an abutment surface that is oriented obliquely to a longitudinal axis of the elongate anchoring portion and the elongate anchoring portion is driven into the one of the adjacent vertebrae with the longitudinal axis thereof oriented at a selected angle relative thereto such that the head portion is positioned between the outer and inner surfaces of the annular wall and the abutment surface is oriented generally orthogonally to an inner facing surface of the one of the adjacent vertebrae when the elongate anchoring portion is fastened thereto to provide a stop to keep the nuclear implant from being expelled through the through opening in the annular wall.

14. A method for restraining a nuclear implant in an intervertebral nuclear space between adjacent upper and lower vertebrae, the method comprising:

creating a through opening in an annular wall into the nuclear space with the through opening having a height less than that of the annular wall extending between the upper and lower vertebrae such that a portion of the annular wall is left intact adjacent one of the upper and lower vertebrae above or below the opening, respectively, and the through opening extends from an outer surface to an inner surface thereof for the full thickness of the annular wall with the wall inner surface extending about the nuclear space to allow insertion of the nuclear implant into the nuclear space;

inserting the nuclear implant through the through opening in the annular wall into the nuclear space so that the nuclear implant traverses the entire thickness of the annular wall for inserting the implant into the nuclear space;

driving an elongate anchoring portion of a single, one-piece fastener into one of the adjacent vertebrae to position a radially enlarged head portion of the single, one-piece fastener in the through opening between the outer and inner surfaces of the annular wall such that the radially enlarged head portion and the intact annular wall portion adjacent the one vertebra cooperate to obstruct an exit path of the implant out from the nuclear space and through the through opening, wherein the elongate anchoring portion of the single fastener is fastened to the one of the adjacent vertebrae at an inner facing surface thereof with a longitudinal axis of the elongate anchoring portion oriented generally obliquely to the inner facing surface.

15. A method for restraining a nuclear implant in an intervertebral nuclear space between adjacent upper and lower vertebrae, the method comprising:

creating a through opening in an annular wall into the nuclear space with the through opening having a height less than that of the annular wall extending between the upper and lower vertebrae such that a portion of the annular wall is left intact adjacent one of the upper and lower vertebrae above or below the opening, respectively, and the through opening extends from an outer surface to an inner surface thereof for the full thickness of the annular wall with the wall inner surface extending about the nuclear space to allow insertion of the nuclear implant into the nuclear space;

inserting the nuclear implant through the through opening in the annular wall into the nuclear space so that the nuclear implant traverses the entire thickness of the annular wall for inserting the implant into the nuclear space;

driving an elongate anchoring portion of a single, one-piece fastener into one of the adjacent vertebrae to position a radially enlarged head portion of the single, one-piece fastener in the through opening between the outer and inner surfaces of the annular wall such that the radially enlarged head portion and the intact annular wall portion adjacent the one vertebra cooperate to obstruct an exit path of the implant out from the nuclear space and through the through opening; and penetrating the intact portion of the annular wall adjacent the one of the upper and lower vertebrae with the elongate anchoring portion of the single fastener such that the intact portion of the annular wall and the head portion of the single fastener positioned in the through opening cooperate to obstruct an exit path of the implant out from the nuclear space through the through opening.

* * * * *